US012285031B2

(12) United States Patent
Kamcharov et al.

(10) Patent No.: US 12,285,031 B2
(45) Date of Patent: *Apr. 29, 2025

(54) BEVERAGE WITH COLLAGEN AND ADDITIONAL ADDITIVES

(71) Applicant: WELLDRINKS LTD, Borough of Lozenents (BG)

(72) Inventors: Alexander Evgenievich Kamcharov, Saint Petersburg (RU); Martin Steele, Dusseldorf (DE); Tihomir Georgiev Yovchev, Borough of Lozenents (BG); Yavor Nikolaev Draganov, Rhodope (BG); Jurgen Pieck, Lutry (CH); Christian Schrobsdorff, Sofia (BG)

(73) Assignee: WELLDRINKS LTD, Borough of Lozenets (BG)

( * ) Notice: Subject to any disclaimer, the term of this patent is extended or adjusted under 35 U.S.C. 154(b) by 77 days.

This patent is subject to a terminal disclaimer.

(21) Appl. No.: 16/680,294

(22) Filed: Nov. 11, 2019

(65) Prior Publication Data

US 2020/0077682 A1 Mar. 12, 2020

Related U.S. Application Data

(63) Continuation-in-part of application No. 16/353,179, filed on Mar. 14, 2019, now abandoned, which is a continuation of application No. 14/969,519, filed on Dec. 15, 2015, now Pat. No. 11,925,192.

(51) Int. Cl.

| | | |
|---|---|---|
| A23L 2/66 | (2006.01) | |
| A23L 2/44 | (2006.01) | |
| A23L 2/52 | (2006.01) | |
| A23L 2/54 | (2006.01) | |
| A23L 2/56 | (2006.01) | |
| A23L 2/58 | (2006.01) | |
| A23L 2/60 | (2006.01) | |
| A23L 2/68 | (2006.01) | |
| A61K 8/65 | (2006.01) | |
| A61K 9/00 | (2006.01) | |
| A61K 38/01 | (2006.01) | |
| A61K 38/39 | (2006.01) | |
| A61Q 19/00 | (2006.01) | |
| A61Q 19/08 | (2006.01) | |

(52) U.S. Cl.
CPC ........ *A23L 2/66* (2013.01); *A23L 2/44* (2013.01); *A23L 2/52* (2013.01); *A23L 2/54* (2013.01); *A23L 2/56* (2013.01); *A23L 2/58* (2013.01); *A23L 2/60* (2013.01); *A23L 2/68* (2013.01); *A61K 8/65* (2013.01); *A61K 38/014* (2013.01); *A61K 38/39* (2013.01); *A61Q 19/007* (2013.01); *A61Q 19/08* (2013.01); *A23V 2002/00* (2013.01); *A61K 9/0095* (2013.01); *A61K 2800/92* (2013.01)

(58) Field of Classification Search
None
See application file for complete search history.

(56) References Cited

U.S. PATENT DOCUMENTS

| | | |
|---|---|---|
| 2003/0175398 A1 | 9/2003 | Ogasawara et al. |
| 2009/0041897 A1 | 2/2009 | Gamay |
| 2010/0316768 A1 | 12/2010 | Stillman et al. |
| 2011/0151059 A1 | 6/2011 | Xu et al. |
| 2014/0212565 A1 | 7/2014 | Bradley et al. |
| 2015/0352045 A1 | 12/2015 | Raper et al. |

FOREIGN PATENT DOCUMENTS

| | | | |
|---|---|---|---|
| CN | 101912132 A | | 12/2010 |
| CN | 102268084 A | | 12/2011 |
| EP | 2088157 | * | 8/2009 |
| ES | 1210813 U | | 4/2018 |
| JP | 2002027956 A | | 1/2002 |
| JP | 2007167079 A | | 7/2007 |
| JP | 2008194010 A | | 8/2008 |
| RU | 2658380 C1 | | 6/2018 |

(Continued)

OTHER PUBLICATIONS

Bio Collagen Powder (Sep. 20, 2012).*
AHS collagen powder-Amazon (First available on Amazon on Jun. 3, 2013).*
Shoseyov et al. ("Human collagen produced in plants"; Bioengineered 5:1, 1-4, Jan/Feb. 2014).*
HSIS.org (https://www.hsis.org/a-z-food-supplements/molybdenum/; May 3, 2008).*
English language translation of JP2007167079 (Google translate).*
Lenntech (https://www.lenntech.com/recommended-daily-intake.htm Jul. 6, 2005).*
Ohara et al. ("Collagen derived dipeptide, proline-hydroxyproline, stimulates cell proliferation and hyaluronic acid synthesis in cultured human dermal fibroblasts" Journal of Dermatology 2010;37:330-338).*

(Continued)

*Primary Examiner* — Julie Ha
*Assistant Examiner* — Tara L Martinez
(74) *Attorney, Agent, or Firm* — Gearhart Law, LLC

(57) ABSTRACT

A beverage comprising a collagen hydrolysate is disclosed. Absorption of the collagen hydrolysate in the intestinal tract can be modulated depending on the molecular weight of the collagen peptides and the presence of certain additives. The optimal concentration of 10,000 dalton collagen hydrolysate for intestinal absorption is about 8.4 g/l which does not appreciably increase even if the collagen concentration is increased to 20, 30 or even 40 g/l in the presence or absence of whey protein. In contrast, the absorption of a 2,000 Dalton collagen hydrolysate composition that does not contain additional proteins is shown to be enhanced by the addition of supplements including vitamins and/or $CO_2$. The absorption is shown to increase with collagen concentration up to an optimal concentration of about 20 g/l. At collagen concentrations greater then about 20 g/l, the absorption of the collagen peptides remains constant, thus the percentage of collagen hydrolysate that is absorbed declines.

13 Claims, 4 Drawing Sheets

(56) References Cited

FOREIGN PATENT DOCUMENTS

| WO | 2004023899 A1 | 3/2004 |
|---|---|---|
| WO | 2007098593 A1 | 9/2007 |
| WO | 2013049540 A2 | 4/2013 |

OTHER PUBLICATIONS

Misako Aito-Inoue, "Transport of a tripeptide, gly-pro-hyp, across the porcine intestinal brush-border membrane," Journal of Peptide Science, 2007, 13, pp. 468-474.

Jeremy M. Berg, et al., New York—W H Freeman; Biochemistry (5th ed), Ch. 23.1.1 (2002).

Jin Ho Chung, et al., "Modulation of skin collagen metabolism in aged and photoaged human skin in vivo," The Journal of Investigative Dermatology, 2001, 117, 5, pp. 1218-1224.

Tomoaki Kawaguchi, et al., "Distribution of prolylhydroxyproline and its metabolites after oral administration in rats," Biol. Pharm. Bull, 2012, 35(3), pp. 422-427.

Jiang Liang, et al., "The protective effects of long-term oral administration of marine collagen hydrolysate from chum salmon on collagen matrix homeostasis in the chronological aged skin of sprague-dawley male rats," Journal of Food Science, 2010, 75(8), pp. H230-H238.

Chintang Liu, et al., "Absorption of hydroxyproline-containing peptides in vascularly perfused rat small intestine in situ.," Biosci Biotechnol Biochem, 2009, 73(8), pp. 1741-1747.

Naoya Matsuda, et al., "Effects of ingestion of collagen peptide on collagen fibrils and glycosaminoglycans in the dermis," J. Nutr. Sci. Vitaminol., 2006, 52, pp. 211-215.

Chisato Oba, et al., "Collagen hydrolysate intake improves the loss of epidermal barrier function and skin elasticity induced by UVB irradiation in hairless mice," Photodermatol Photoimmunol Photomed, 2013, 29, pp. 204-211.

Hiroki Ohara, et al., "Collagen-derived dipeptide, proline-hydroxyproline, stimulates cell proliferation and hyaluronic acid synthesis in cultured human dermal fibroblasts," Journal of Dermatology, 2010, 37, pp. 330-338.

I. Pasquali-Ronchetti, et al., "Elastic Fiber During Development and Aging," Microscopy Research and Technique, 1997, 38, pp. 428-435.

Taihao Quan, et al., "Elevated matrix metalloproteinases and collagen fragmentation in photodamaged human skin—impact of altered extracellular matrix microenvironment on dermal fibroblast function," J. Invest. Dermatol., 2013, 133 (5), pp. 1362-1366.

John R. Ross, et al., "The Effect of Dehydration on the Pancreatic and Intestinal Enzymes" The Department of Medical Research, Bunting Institute, University of Toronto, Toronto, Canada (1933).

A.M. Kligman, et al., "The anatomy and pathogenesis of wrinkles.," British Journal of Dermatology, 1985, 113, pp. 37-42.

Shingo Sakai, et al., "Hyaluronan exists in the normal stratum corneum," The Society for Investigative Dermatology, Inc., 2000, 114, 6, pp. 1184-1187.

Silke K. Schagen, et al., "Discovering the link between nutrition and skin aging," Dermato-endocrinology, 2012, 4 (3), pp. 298-307.

Yasutaka Shigemura, et al., "Dose-dependent changes in the levels of free and peptide forms of hydroxyproline in human plasma after collagen hydrolysate ingestion," Food Chemistry, 2014, 159, pp. 328-332.

Jun Shimizu, et al., "Oral collagen-derived dipeptides, prolyl-hydroxyproline and hydroxyprolyl-glycine, ameliorate skin barrier dysfunction and alter gene expression profiles in the skin," Biochemical and Biophysical Research Communications, 2015, 456, pp. 626-630.

Mari Watanabe-Kamiyama, et al., "The influence of age and sex on skin thickness, skin collagen and density," J. Agric. Food Chem., 2010, 58(2), pp. 835-841.

James Varani, et al., "Decreased collagen production in chronologically aged skin—roles of age-dependent alteration in fibroblast function and defective mechanical stimulation," American Journal of Pathology, 2006, 168(6), pp. 1861-1868.

Sylvie Verdier-Sevrain, "Skin hydration—a review on its molecular mechanisms," J Cosmet Dermatol, 2007, 6(2), pp. 75-82.

Mari Watanabe-Kamiyama, et al., "Absorption and effectiveness of orally administered low molecular weight collagen hydrolysate in rats," J Agric Food Chem, 2010, 58(2), pp. 835-841.

Extended European Search Report issued Jul. 16, 2018 in corresponding European application No. 15877721.9, consisting of 10 Pages.

Tomoko Okawa et al., "Oral administration of collagen tripeptide improves dryness and pruritus in the acetone—induced dry skin model", Journal of Dermatological Science, Elsevier, Amsterdam, NL; vol. 66, No. 2. Feb. 8, 2012, pp. 136-143.

Anonymous: "Cocoa Fruit Flavored Collagen Enhanced Sport Still Water", Nov. 1, 2014, URL: http://www.gnpd.com/sinatra/recordpage/2764481.

Anonymous: "EpiQ NAG Collagen Beverage", Dec. 1, 2014, URL: http://www.gnpd.com/sinatra/recordpage/2829239.

Katarzyna Dybka, et al., "Collagen hydrolysates as a new diet supplement," Food Chemistry and Biotechnology, 2009, 73(1058), pp. 83-92.

L. Mark Hanover, et al., "Manufacturing, composition and applications of fructose," Am. J. Clin. Nutr., 1993, 58 (Suppl): pp. 724s-32s.

Menon Rekha Ravindra, et al., "Carbonated fermented dairy drink-effect on quality and shelf-life," J. Food. Sci. Technol., 2014, 51(11), pp. 3397-3403.

Matheson, "Recommended Gas Mixtures for Food and Beverage Packaging," Matheson Tri-Gas, Inc., 2014, pp. 1-4.

Written Opinion of the International Searching Authority, dated Mar. 23, 2021, for corresponding PCT Application No. PCT/IB2020/060620, International Filing Date of Nov. 11, 2020, consisting of 6 Pages.

International Search Report, dated Mar. 23, 2021, for corresponding PCT Application No. PCT/IB2020/060620, International Filing Date of Nov. 11, 2020, consisting of 11 Pages.

\* cited by examiner

Beverage with Collagen and Additional Additives

Beverage with Collagen and Additional Additives

FIGURE 1C

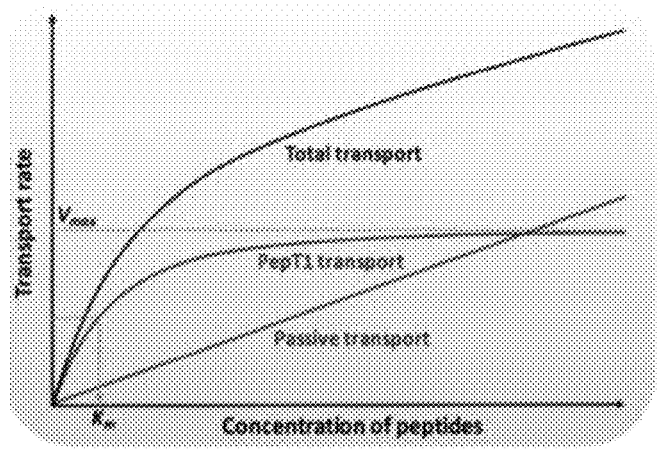

Optimal Dose. Optimal DV dose of targeted vitamins and minerals (at this optimal dose "Vitamin Package") for absorption of collagen hydrolysate via Hydrolyzed Collagen Beverage (500 ml. beverage is 1 dose) permitting maximum absorption without formation of sediment and without significant effect on beverage taste.

|  | Magnesium mg/d | Manganese mg/d | B12 mcg/d | B6 mg/d | B7 mcg/d | Zinc mg/d | Vit. C mg/d |
|---|---|---|---|---|---|---|---|
| RDA-DV | 400 | 2.0 | 6.0 | 2.0 | 300 | 15 | 60 |
| Optimal % DV per 500 ml dose | 10% | 10% | 10% | 10% | 10% | 10% | 10% |
| 10% | 40 | 0.4 | 0.6 | 0.4 | 30 | 1.5 | 6.0 |

FIGURE 2

Beverage with Collagen and Additional Additives

| Scenarios | g/l 8.4 | | g/l 10 | | g/l 20 | | g/l 30 | | g/l 40 | |
|---|---|---|---|---|---|---|---|---|---|---|
| | g. absorb per l. | % | g. absorb per l. | % | g. absorb per l. | % | g. absorb per l. | % | g. absorb per l. | % |
| LCP collagen hydrolysate, 10,000 Da. (*with whey protein*) | 4.09 | 48.70% | 4.91 | 49.10% | 9.78 | 48.90% | 9.78 | 32.60% | 9.78 | 24.45% |
| LCP collagen hydrolysate, 10,000 Da.** (** = *without other proteins*) | 4.95 | 58.90% | 5.92 | 59.20% | 11.90 | 59.50% | 11.90 | 39.67% | 11.90 | 29.75% |
| LCP collagen hydrolysate, 2,000 Da** | 5.83 | 69.40% | 6.88 | 68.80% | 13.86 | 69.30% | 13.86 | 46.20% | 13.86 | 34.65% |
| LCP collagen hydrolysate, 2,000 Da., carbonated to 6.2 g/l | 6.56 | 78.10% | 7.87 | 78.70% | 15.90 | 79.50% | 15.90 | 53.00% | 15.90 | 39.75% |
| LCP collagen hydrolysate, 2,000 Da.**, carbonated 6.2 g/l, and "*Vitamin Package*" | 7.04 | 83.80% | 8.43 | 84.30% | 16.94 | 84.70% | 16.94 | 56.47% | 16.94 | 42.35% |
| HCP collagen hydrolysate, 2,000 Da.**, carbonated 6.2 g/l, and "*Vitamin Package*" | 7.49 | 89.20% | 8.89 | 88.90% | 17.94 | 89.70% | 17.94 | 59.80% | 17.94 | 44.85% |

FIGURE 3

Beverage with Collagen and Additional Additives

BEVERAGE WITH COLLAGEN AND ADDITIONAL ADDITIVES

CROSS-REFERENCE TO RELATED APPLICATIONS

This application is a continuation-in-part application of U.S. patent application Ser. No. 16/353,179, filed Mar. 14, 2019, which is a continuation of U.S. patent application Ser. No. 14/969,519, filed Dec. 15, 2015, which claims priority to Bulgarian Utility Model No. 2935 filed on Jan. 16, 2015. The content of each of the aforementioned applications is incorporated by reference herein in their entireties.

FIELD OF THE EMBODIMENTS

This invention characterizes beverages comprising hydrolyzed collagen, derived from animal raw materials. Those raw materials may vary according to their origin, including mammals, fish, birds, snails; or from various parts of a carcass.

BACKGROUND OF THE EMBODIMENTS

Many of the beneficial properties of collagen are applicable both to the medical field and cosmetics. Collagen is a major protein of the human connective tissue including, for example, cartilage, cornea, arteries, and skin. Robust and inextensible, collagen possesses great tensile strength. It is the principal component of cartilage, tendons, articular joints, bone as well as teeth. Collagen can also be found in the walls of capillaries, veins and arteries. It imparts to them strength and elasticity for the effective transport of blood throughout the body. Collagen is of vital importance for muscle function. The collagen molecules also provide muscle fibers with strength and structure necessary for their functioning over long periods of time. Collagen not only supports skeletal muscle fibers, but also smooth muscles present in cardiac, bladder and genital muscles.

Collagen is permanently being replaced in the human body. However, after the age of 25 this process decelerates and progressively slackens with advancing age. Disorders of collagen buildup can also be provoked in situations of permanent overloading (for example in power sports, or in case of intensive physical activity). With aging, the amount of de novo synthesized collagen is reduced as result of a slowdown in metabolism which results in a gradual decline in the resilience of both soft tissues and bones (osteoporosis). The collagen deficit due to advancing age, leads to visible effects including skin drying and wrinkling, limited mobility due to stiffness and joint pain, bone fractures caused by osteoporotic changes, the appearance of pointed and visible capillaries on the skin surface, as well as the appearance of varicose veins.

Specific references to relevant prior art are herein described as follows:

U.S. Patent Publication No. 2010/0316768 and International Patent Publication No. WO2004023899 disclose a shelf-stable, ready to use, water-like composition for humans/animals; as an adjunct to fiber-water, and/or safe drinking water, consumed directly, tube feedings, or in the preparation/reconstitution of food(s)/beverage(s). These disclosures teach a fortified fiber-water with added delivery systems: Encapsulations/particles, of different size(s), shape(s), material(s), colors, non-visible, serving one or more functions: improved taste, odor-masking; controlled release applications; bio-availability of actives, avoid hygroscopicity; minimized interactions, improved thermal, oxidative, and shelf-life; decorative.

U.S. Patent Publication No. 2014/0212565 and International Patent Publication No. WO2013049540 teach a clear high protein beverage comprising water; between about 4% and about 8% by weight protein; and a flavoring. WO2007098593 teaches an alkaline soluble fiber compositions and methods for preparing the same. Soluble fiber for use in the compositions of the invention is contributed from one or more sources and is preferably inulin, FOS and/or scFOS. In some cases, the compositions have a pH of between 8.0 and 9.5.

The method and solutions known in the art fail to remedy all the problems taught by the present disclosure. There is an ongoing unmet need in the art for improved methods of restoring collagen lost as a result of aging.

SUMMARY OF THE EMBODIMENTS

The preferred embodiments of the present invention will now be described. Reference will now be made in detail to each embodiment of the present invention. Such embodiments are provided by way of explanation of the present invention, which is not intended to be limited thereto. In fact, those of ordinary skill in the art may appreciate upon reading the present specification that various modifications and variations can be made thereto.

The disclosure described a hydrolyzed collagen beverage that facilitates the absorption of the hydrolyzed collagen in the digestive tract.

In a first aspect, a beverage is disclosed consisting of a non-protein portion comprising water, and a protein portion consisting of collagen.

In certain embodiments of the first aspect, the collagen is from non-human animals.

In certain embodiments of the first aspect, the collagen is isolated from a plant expressing recombinant collagen.

In certain embodiments of the first aspect, the collagen is hydrolyzed.

In certain embodiments of the first aspect, the hydrolyzed collagen comprises peptides having a molecular weight of no more than about 2000 daltons.

In certain embodiments of the first aspect, the collagen concentration range is between 1 milligram/liter to about 8440 milligram/liter.

In certain embodiments of the first aspect, the collagen concentration range is between about 8440 milligram/liter and 40 g/liter In certain embodiments of the first aspect, the water is carbonated.

In certain embodiments of the first aspect, the non-protein portion of the beverage does not comprise sodium acid sulphate.

In certain embodiments of the first aspect, the non-protein portion of the beverage does not comprise any one of citric acid, phosphoric acid, malic acid, tartaric acid and fumaric acid.

In certain embodiments of the first aspect, the non-protein portion of the beverage further comprises a vitamin.

In certain embodiments of the first aspect, the vitamin is in an amount equal to the US "Recommended Daily Allowance (RDA)."

In certain embodiments of the first aspect, the vitamin comprises at least one of Vitamin A, Vitamin D, Vitamin E, Vitamin K, Vitamin C, Thiamin (Vitamin B1), Riboflavin (Vitamin B2), Niacin (Vitamin B3), Vitamin B6, Folic acid (Vitamin B9), Vitamin B12, Biotin (Vitamin B7), Pantothenic acid (Vitamin B5).

In certain embodiments of the first aspect, the vitamin comprises any one of Vitamin B6, Biotin (Vitamin B7), Vitamin C and Vitamin B12.

In certain embodiments of the first aspect, the vitamin comprises any two of Vitamin B6, Biotin (Vitamin B7), Vitamin C and Vitamin B12.

In certain embodiments of the first aspect, the vitamin comprises any three of Vitamin B6, Biotin (Vitamin B7), Vitamin C and Vitamin B12.

In certain embodiments of the first aspect, the vitamin consists of Vitamin B6, Biotin (Vitamin B7), Vitamin C and Vitamin B12.

In certain embodiments of the first aspect, the non-protein portion of the beverage further comprises a mineral.

In certain embodiments of the first aspect, the mineral is chosen from at least one of Potassium (K), Chloride (Cl), Calcium (Ca), Phosphorus (P), Magnesium (Mg), Iron (Fe), Zinc (Zn), Copper (Cu), Manganese (Mn), Fluoride (F), Selenium (Se), Chromium (Cr), Molybdenum (Mo) and Iodine (I).

In certain embodiments of the first aspect, the mineral consists of manganese and/or magnesium.

In certain embodiments of the first aspect, the non-protein portion of the beverage comprises water, a vitamin and a mineral.

In certain embodiments of the first aspect, the mineral is manganese and/or magnesium.

In certain embodiments of the first aspect, the vitamin is Vitamin B6, Biotin (Vitamin B7), Vitamin C and Vitamin B12.

In a second aspect, a beverage is disclosed comprising a non-protein portion comprising water, and a protein portion, wherein the protein portion comprises hydrolyzed collagen and no whey protein.

In a third aspect, a beverage is disclosed consisting of water and hydrolyzed collagen.

In certain embodiments of the third aspect, the beverage has a pH of about 6.8.

In a fourth aspect, a method of increasing the absorption of hydrolyzed collagen in the digestive tract of a subject is disclosed comprising any one of the aforementioned beverages.

In certain embodiments, a beverage is disclosed having water and a concentration range of about 0.001 grams per liter to 8.44 grams per liter of collagen, wherein the collagen is hydrolyzed. The collagen concentration range may be between 1 milligram per liter to about 8440 milligram per liter or 1 part per million to about 8440 parts per million. The hydrolyzed collagen can have collagen peptides produced through hydrolysis of a plurality of collagen from a variety of sources, including, for example, animal raw materials, animals raised in non-organic or organic farms, animals from various animal species and various parts of the animal carcass. In certain embodiments, collagen, as used herein, can be recombinant collagen that is expressed for example in plants, yeast, tissue culture cells or bacteria. In certain embodiments, the beverage contains water including, for example, tap water, spring or mineral water. In certain embodiments, the beverage may be carbonated or non-carbonated.

In certain embodiments, a beverage is disclosed having water, a concentration range of about 0.001 grams per liter to 8.44 grams per liter of collagen; and at least one additive. In certain embodiments, the additive may comprise a stabilizing preservative. The stabilizing preservative may have chemical substances which dissolve in the beverage and are only parts of its content or have chemically active substances used in the production of the beverage but subsequently dissolve to other ingredients. In certain embodiments, the additive may comprise a preservative. In certain embodiments, the beverage may be pasteurized. In certain embodiments, the additive may comprise a packaging gas and/or a colorant. The colorant may be synthetic or organic and derived from vegetable, fruit or animal origin. The colorant may have a concentration range of at least one of 0.0001% to about 0.05%, 0.001% to about 0.1%, and 0.003% to about 0.2%. In certain embodiments, the additive may comprise a plurality of sweeteners. The sweeteners may be in liquid form, hard form, natural sugars, refined sugars, low caloric, and non-refined sugars. In certain embodiments, the additive may comprise a plurality of fruit juices or fruit juice concentrates. In certain embodiments, the additive may comprise a plurality of acidity regulating or E-number additives. In certain embodiments, the additive may comprise a thickener, flavor enhancers, vitamins, minerals, electrolytes and/or amino acids. The additive may be at least one other protein with a concentration range sum total of 0.0001 grams per liter to 8.44 grams per liter. In certain embodiments, the additive may comprise a dairy component, probiotic ingredients and/or extracts. In certain embodiments, the beverage may be carbonated or non-carbonated.

In certain embodiments, absorption of the collagen hydrolysate in the intestinal tract can be modulated depending on the molecular weight of the collagen peptides and the presence of certain additives. The optimal concentration of 10,000 dalton collagen hydrolysate for intestinal absorption is about 8.4 g/l which does not appreciably increase even if the collagen concentration is increased to 20, 30 or even 40 g/l in the presence or absence of whey protein. In contrast, the absorption of a 2,000 dalton collagen hydrolysate composition, that does not contain whey protein, is shown to be enhanced by the addition of supplements including vitamins and/or $CO_2$ and/or pro-hyp/hyp-gly. The absorption is shown to increase with collagen concentration up to an optimal concentration of about 20 g/l. At collagen concentrations greater than about 20 g/l, the absorption of the collagen peptides is maintained or decreases.

BRIEF DESCRIPTION OF THE DRAWINGS

FIG. 1C shows an exemplary embodiment of peptide transport across a Caco 2 cell monolayer as a function of collagen peptide concentration;

FIG. 2 shows an exemplary embodiment of the optimal DV (daily value) dose of Vitamin Package elements for absorption via Hydrolyzed Collagen Beverage (500 ml. beverage is 1 dose);

FIG. 3 shows an exemplary embodiment of collagen hydrolysate beverage on absorption;

DETAILED DESCRIPTION OF THE INVENTION

Figure 1A:
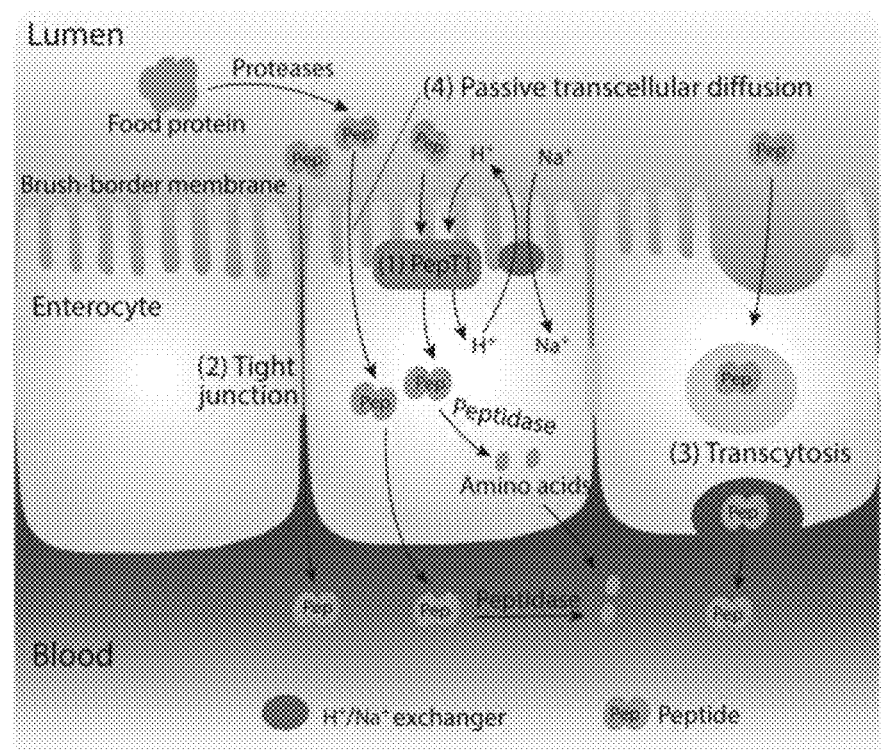
FIG. 1A is an exemplary schematic showing how peptides are absorbed across the intestinal wall.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, the materials, methods, and examples are illustrative only and not intended to be limiting. Other features of the disclosure are apparent from the following detailed description and the claims.

Definitions

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" or a range "between 1 ng and 5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3- 5 ng, and 4-5 ng.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As used herein, Hyp refers to hydroxyproline.

As used herein, the term "isolated" refers to a sample in a non-naturally occurring state outside an organism (e.g., isolated from organism or a biological sample from an organism).

A "subject" is a vertebrate, preferably a mammal (e.g., a non-human mammal), more preferably a primate and still more preferably a human. Mammals include, but are not limited to, primates, humans, farm animals, rodents, sport animals, and pets.

As used herein, a "Vitamin Package" refers to the core vitamin/mineral additive package (see FIG. 2) which aids in absorption of higher percentages of collagen hydrolysate in a hydrolyzed collagen beverage and will be set at the concentrations specified in FIG. 2. The specific dose set out delivers the optimal dose of vitamins to absorption of collagen hydrolysate via Hydrolyzed Collagen Beverage (one 500 ml. beverage is 1 dose) to allow maximum absorption while avoiding formation of sediment and without significant effect on beverage taste. These core vitamins will always be part of the Vitamin package. Other vitamins and minerals can be added without negatively affecting collagen absorption. Additional vitamins/minerals or increased concentration may, however, may have a significant effect on product taste and may cause the formation of sediment in the beverage.

As used herein, RDA is the acronym for "Recommended Daily Allowance."

As used herein, the maximum RDA refers to the estimated Maximum percentage of RDA of elements of the Vitamin Package which could be effectively absorbed via a hydrolyzed collagen beverage.

In its original state, the digestive system is incapable of enzymatically degrading collagen in part because to its great length and the crosslinking between collagen fibers. Thus, administration of collagen to an individual is best achieved using "hydrolyzed" collagen that facilitates its absorption in the digestive tract. Collagen can be administered in the form of tablets, capsules, or in the form of a drink.

Recent scientific studies show, that drinking collagen in liquid form results in more than 90% absorption of collagen in the digestive tract, which is absolutely unachievable when collagen is either in tablet or capsule form. The liquid collagen form has demonstrated better results, higher efficiency of active ingredients and unrivalled absorption. Moreover, all dietary supplement forms—tablets, capsules, sachets etc. definitely burden more on the digestive system, in contrast to the liquid form for drinking, which is easily assimilated by the stomach. The accurate dosage is of particular importance for the consumers of collagen drinks.

Known collagen drinks have a different percentage of hydrolyzed collagen and include many additives like stabilizers, preservatives, aromatizers, artificial colors, flavor enhancers etc. These components are put in products with more concentrated amount of added hydrolyzed collagen. Because of the absence of any additional components, except drinking water and hydrolyzed collagen, the disclosed beverage represents an important benefit, which ensures its administration without limitations regarding age and health state of the expected consumers.

The risk of forming intolerance, or exacerbation of hyperesthesia of the organism, which normally is provoked by additionally added unnatural chemical additives, is completely avoided.

In certain embodiments of the present invention, the optimal concentration of hydrolyzed collagen in the drink is completely clear in taste and almost wholly corresponding to the neutral taste of the clean drinking water. Furthermore, the drink is maximal simplified in functionally and that is why it doesn't burden the consumer with additional calories. As a whole, the consumption of the created non-carbonated alcohol-free drink leads to the improvement of the skin structure, the skin density, skin turgor, muscle tone as well as to the improvement of the condition and the flexibility of a subject's joints.

In certain embodiments, the hydrolyzed collagen drink can be the sole source of a subject daily intake of water.

The market offers a wide variety of beverages containing various healthy ingredients. Contemporary society strives to improve its nutrition by selecting food and beverages with high added value, provided by the various forms of ingredients, beneficial for the body, included in their contents. This way, the need of consumers to reach better shape and tonus, to live a full life, feel good and preventively enhance their health can be satisfied. Beverages, which include in their content hydrolyzed collagen, may be offered in convenient and easy for consumption form. The collagen in these drinks may be a source of valuable proteins in the body that can characterize with high and full assimilation. At the same time, when collagen is added in beverages, it combines the advantage, the daily intake of fluids to be stimulated, which usually is what underlies most recommended healthy diets. The sufficient intake of fluids is extremely important for many groups of people having specific and increased needs of fluids, such as, active athletes or people whose work and life comprise high physical activity or mental pressure. The additional intake of hydrolyzed collagen is a valuable source of one's daily nutrition. Also, collagen offers one a full set of all amino acids needed for the synthesis of collagen matrix in the human body. This is particularly important for active people, the elderly, pregnant and lactating women, people undergoing aesthetic surgery and others In certain embodiments of the present invention beverages are disclosed comprising functional ingredient hydrolyzed collagen in concentration: from 0.001 g/L to 8.44 g/L, which may also be expressed as: from 1 ppm to 8440 ppm. This concentration of hydrolyzed collagen in the beverages shall be reviewed regarding ready for consumption beverages or regarding beverages obtained after dilution by adding additional water in the prescribed proportion to produced concentrates in the form of powder or liquids. The functional ingredient hydrolyzed collagen, also known as collagen peptides, is produced through hydrolysis in controlled conditions of raw materials such as collagen sources from various animal origin.

In certain embodiments, the disclosed beverage comprises hydrolyzed collagen at a concentration of about 0.01-1 g/l, about 0.01-2 g/l, about 0.01-3 g/l, about 0.01-4 g/l, about 0.01-5 g/l about 0.01-6 g/l, about 0.01-7 g/l, about 0.01-8 g/l, about 0.01-9 g/l, about 0.01-10 g/l, about 0.01-11 g/l, about 0.01-12 g/l, about 0.01-13 g/l, about 0.01-14 g/l, about 0.01-15 g/l, about 0.01-16 g/l, about 0.01-17 g/l, about 0.01-18 g/l, about 0.01-19 g/l or about 0.01-20 g/l, about 0.01-21 g/l, about 0.01-22 g/l, about 0.01-23 g/l, about 0.01-24 g/l, about 0.01-25 g/l, about 0.01-26 g/l, about 0.01-27 g/l, about 0.01-28 g/l, about 0.01-29 g/l, about 0.01-30 g/l, about 0.01-31 g/l, about 0.01-32 g/l, about 0.01-33 g/l, about 0.01-34 g/l, about 0.01-35 g/l, about 0.01-36 g/l, about 0.01-37 g/l, about 0.01-38 g/l, about 0.01-39 g/l or about 0.01-40 g/l or more.

In certain embodiments, the disclosed beverage comprises hydrolyzed collagen having a molecular weight of 1-10000, 1-9000, 1-8000, 1-7000, 1-6000, 1-5000, 1-4000, 1-3000, 1-2000, 1-1000 or 1-500.

In certain embodiments, the disclosed beverage comprises hydrolyzed collagen having a molecular weight between 10000-500, 10000-1000, 10000-2000, 10000-3000, 10000-4000, 10000-5000, 10000-6000, 10000-7000, 10000-8000, 10000-9000 or 10000-9500.

In certain embodiments, the disclosed beverage comprises hydrolyzed collagen having a molecular weight of about 500, about 1000, about 2000, about 3000, about 4000, about 5000, about 6000, about 7000, about 8000, about 9000 or about 10000.

In certain embodiments, the disclosed beverage comprises hydrolyzed collagen at a concentration of at least 1 g/l, at least 2 g/l, at least 3 g/l, at least 4 g/l, at least 5 g/l, at least 6 g/l, at least 7 g/l, at least 8 g/l, at least 9 g/l, at least 10 g/l, at least 11 g/l, at least 12 g/l, at least 13 g/l, at least 14 g/l, at least 15 g/l, at least 16 g/l, at least 17 g/l, at least 18 g/l, at least 19 g/l or at least 20 g/l.

In certain embodiments, the disclosed beverage comprises hydrolyzed collagen at a concentration of no more than about 20 g/l.

In certain embodiments, the disclosed beverage comprises 2000 Dalton hydrolyzed collagen at a concentration of no more than about 20 g/l.

The beverages containing hydrolyzed collagen characterize with great diversity, depending on the other combined ingredients that they may include. Beverages may contain only hydrolyzed collagen and water.

In certain embodiments, the water for producing the beverages may be tap water or spring or mineral water or water, gained by icebergs (glaciers). When tap water is used, the tap water shall mandatorily be supplied by central water supply system or extracted underground water or extracted from natural or artificially constructed ponds. Also, preventively or in case of need, the water can be additionally purified, or processed approved by the appropriate healthcare authority's methods of additional purification or processing:

Examples of such methods are:
mechanical filtration through filtration systems,
filtration through chemically active filters to separate the unwanted salts of iron (Fe) and manganese (Mn),
decrease of total mineralization through ultrafiltration—using ultrafiltration (reverse osmosis systems;
decrease of total mineralization through filtration in ion exchange filter systems,
decrease of total mineralization through distillation of water (evaporation and further condensation),
decontamination by UV-filter (UV-lamps),
decontamination by using chemical processing agents such as chlorine ($Cl_2$), chlorine dioxide ($ClO_2$), ozone ($O_3$), active oxygen ($O_2$) and others.

Also, water, used for the beverages may be additionally carbonated through adding Carbon Dioxide—$CO_2$. The quantity of the Carbon Dioxide added may reach 7.0 volume units (7.0 v/v). In the most common beverages combination, it may usually vary between 0.5 and 5.0 v/v.

In certain embodiments, beverages containing hydrolyzed collagen may be produced by stabilizing preservatives. The preservatives used shall be permitted for use for the category of beverages. Respectively, the preservatives may be chemical substances (as Potassium Sorbate [E202], Sodium benzoate [E211] and others), which dissolute in the product and are only parts of its content or may be chemically active substances, used in the production of the product but subsequently dissolute to other ingredients (such as Dimethyl dicarbonate [E242]).

In certain embodiments, beverages containing hydrolyzed collagen may be produced without any preservatives as well as their stabilization in those cases is ensured through applying appropriate technological production methods.

Such methods are for example:
pasteurization of the product in combination with a "clean fill" and subsequent storage at refrigeration conditions,
pasteurization of the product by UHT-sterilization followed by aseptic filling (filling in sterile environment) of the product;
pasteurization of the product followed by hot filling of the product,
filling of the product and further tunnel pasteurization ensuring reaching commercial sterility of the product;
pasteurization of the product and using special nanomaterials when packaging the product in combination with further storage at refrigerator conditions.

In certain embodiments, in the process of filling the beverages, regardless of whether the beverage is produced by adding preservatives or with no added preservatives, packaging gases may be used and added in the package prior to filling, during the filling or after it. Packaging gases are gases, different than air, and are inert gases such as: Nitrogen [E941], Carbon dioxide [E290], Helium [E939] and others. These gases are added in the filling process with the purpose of protecting the product from adverse processes such as oxidation, change in taste, aroma and appearance. These gases contribute to ensuring the shelf life of the product while helping to preserve the quality of the added nutrients.

In certain embodiments, beverages containing hydrolyzed collagen may be colourless or coloured, clear or cloudy and may contain a fine precipitate of larger particles on the bottom and/or to have uniformly dispersed particles in the liquid. They may be calm fluids or carbonated.

In certain embodiments, beverages containing hydrolyzed collagen that may be colored, various colorants may be added such as synthetic or organic ones from vegetable or animal origin or may be from various fruit and/or vegetable concentrates, vegetable extracts. Added colourants, classified as additives with an E-number may be permitted for use in the beverage. The exact amount of coloring agent used will vary, depending on the agents used and the intensity desired in the finished product. Generally, if utilized, the coloring agent should be present at a level of from about 0.0001% to about 0.5%, from about 0.001% to about 0.1%, or from about 0.003% to about 0.2%, by weight or volume of the composition. Certain formulations will have no added colorant.

In certain embodiments, beverages containing hydrolyzed collagen may be produced unsweetened or sweetened through adding various sweeteners or mixtures of several ones.

In certain embodiments, sweetening the present beverage may be achieved by adding sweeteners, most of which are low-calorie ones. Liquid as well as hard sweeteners may be used such as crystals or granules. Examples for sweeteners include:
in a liquid form are the polyols: Sorbitol (E420), Xylitol [E967], Mannitol [E421], Maltitols [E965] and others,
in a hard form are: Aspartame [E951], Cyclamates [E952], Neotame [E961], Acesulfame K [E950] and others, In certain embodiments, sweetening beverages may be achieved by adding various types of sugars derived from natural sources. These sugars may be respectively non-refined or refined to a various extend. Examples of such sugars are: refined white sugar, unrefined or partly refined sugar, honey, fructose, glucose, glucose-fructose syrups, syrups derived from fruits, plant extracts.

In certain embodiments, the desired degree of sweetness of the present invention's beverage may vary from ° Bx=1.0÷16.0 (brix units) or in cases when using artificial or natural low caloric sweeteners, the desired sweetness intensity shall match equivalences of ° Bx=1.0÷16.0 for ready to drink beverages. One brix unit (° Bx) corresponds to 1% water aqueous sugar solution, i.e. 1.0 g sugar per 100 ml water.

In certain embodiments, for regulating the acidity and/or giving a sour taste of beverages containing hydrolyzed collagen, fruit juices or fruit juice concentrates may be added. These fruit juices may have a sour taste, acidity regulating additives, or E-number additives such as, Citric acid [E330], Phosphoric acid [E338], Phosphates [E339; E340; E341, E343], Citrates [E331; E332; E333] and others. The titratable acidity of a preferred embodiments of the present invention's beverage containing hydrolyzed collagen may be a value within the range of from about 0.01% w/v to about 0.85% w/v, about 0.1% w/v to about 0.45% w/v, 0.12% w/v to about 0.35% w/v or any ranges or single values within these ranges.

In certain embodiments, for beverages containing hydrolyzed collagen, other ingredients may be added such as: thickeners and/or stabilizers. Thickeners are substances which increase the viscosity of a foodstuff. Stabilisers are substances which make it possible to maintain the physico-chemical state of a foodstuff. Stabilisers include substances which enable the maintenance of a homogenous dispersion of two or more immiscible substances in a foodstuff. Substances which stabilise retain or intensify an existing colour of a foodstuff and substances which increase the binding capacity of the food by the formation of cross-links between proteins. Example for ingredients used as thickeners and stabilizers are the substances: Gum arabic [E414], Guar gum [E412], Carrageenan [E407], Pectins [E440] and others.

In certain embodiments, for enhancing and modifying the intensity of taste of the present invention's beverage containing hydrolyzed collagen, ingredients such as flavour enhancers may be added. These are substances which enhance the existing taste and/or odour of a foodstuff. Such are for example: Glutamic acid [E620], Guanylic acid [E626], Inosinic acid [E630] and others. For the purpose of adding flavour for taste, organic substances may be added to the present invention's beverage. Such organic substances include, for example: table salt, extracts and tinctures of plants, fruit, seeds, yeast extract and others.

In certain embodiments, fruit and vegetable juices, fruit and vegetable puree, concentrates from fruit and vegetables as well as extracts or tinctures of fruit, part of fruit or plants may all be added to the present invention's hydrolyzed collagen beverage or it may contain such substances. The diversity of this category of additives is high as it is conditioned on the natural diversity of plants. The juices, purees, concentrates or extracts that may be added to the present invention's beverage may be clear or cloudy, contain particles of fruit, vegetables or plants as seeds, parts of the peel, pulp, cells and so on. An example of clear juices that can be added to the present invention's beverage may be juices made from: apples, cherries, raspberries, strawberries, lemon, orange, grapefruit etc. Cloudy juices and purees can be produced from fruits: apple, sour cherry, raspberry, lemon, orange, plum, pear, apricot, peach, etc. In certain embodiments, the beverage containing hydrolyzed collagen disclosed here may optionally include one or more juices (e.g., one or more of single-strength fruit, berry, or vegetable juice, as well as extracts, concentrates, purees, milks, and other forms) present at a level from about 0.0005% to about 99.16%, about 0.001% to about 20%, about 0.005% to about 15%, about 0.01% to about 10%, about 0.05% to about 5%, about 0.01% to about 10%, about 0.05% to about 5%, or about 0.1% to about 2.5% by weight of the beverage, or at a level of about 0.001%, 0.0025%, 0.005%, 0.0075%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0 or about 99.16%, about by weight of the beverage, or any ranges or single values within these ranges. Typically, juice can be used, if at all, in an amount of from about 0.001% to about 45% by weight. Fruit and vegetable juices, fruit and vegetable puree, concentrates from fruit and vegetables as well as extracts or tinctures of fruit, part of fruit or plants may be mixed in all possible combinations with each other and then added to the present invention's hydrolyzed collagen beverage In certain embodiments, for flavouring the present invention's beverage, aromas as well as ingredients with flavouring properties may be added. The beverage containing hydrolyzed collagen disclosed here may optionally contain one or more flavourings or flavour compositions. For example, natural and/or synthetic fruit flavours, botanical flavours, other flavours, and mixtures thereof. Added concentrated aromas may be extracted from natural sources as: fruit, food, parts of plants, smoke and so on but may also consist of synthetic flavourings, approved for use with foodstuff. For flavouring the present invention's beverage, ingredients with flavouring properties such as herbs and spices extracts, fruit extracts and fruit concentrates with intense aroma may be used.

In certain embodiments, the present invention's hydrolyzed collagen beverage disclosed here may optionally include one or more flavourings present at a level from about 0.0005% to about 5%, about 0.001% to about 4%, about 0.005% to about 3%, about 0.01% to about 2%, about 0.05% to about 1%, or about 0.1% to about 0.5% by weight of the beverage, or at a level of about 0.001%, 0.0025%, 0.005%, 0.0075%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or about 1.0% by weight of the beverage, or any ranges or single values within these ranges.

In certain embodiments, vitamins and minerals with the purpose of enriching their nutritional value may be added to the present invention's beverage. Vitamins include, but are not limited to, Vitamin A, Vitamin D, Vitamin E, Vitamin K, Vitamin C, Thiamin (Vitamin $B_1$), Riboflavin (Vitamin $B_2$), Niacin (Vitamin $B_3$), Vitamin $B_6$, Folic acid (Vitamin $B_9$), Vitamin $B_{12}$, Biotin (Vitamin $B_7$), Pantothenic acid (Vitamin $B_5$). Minerals include, but are not limited to, Potassium (K), Chloride (Cl), Calcium (Ca), Phosphorus (P), Magnesium (Mg), Iron (Fe), Zinc (Zn), Copper (Cu), Manganese (Mn), Fluoride (F), Selenium (Se), Chromium (Cr), Molybdenum (Mo), Iodine (I).

In certain embodiments, supplements are typically present in amounts generally accepted under good manufacturing practices and are typically present in amounts between about 7.5% to about 100% RDV, where such RDV are established. But may present at a level from about 101% to about 150% RDV, about 120% to about 200% RDV, about 150% to about 300% RDV, about 200% to about 500% RDV.

In certain embodiments, vitamins and minerals are used to enrich the beverage nutritional profile. For example, according to legislative food sources, a good source of Vitamin A can be found in substances such as: retinol, retinyl acetate, retinyl palmitate, beta-carotene. As Magnesium (Mg) sources used may be: magnesium carbonate, magnesium chloride, magnesium gluconate and etc. may be added to the present invention's beverage.

In certain embodiments, enrichment of beverages with vitamins and minerals may be done with organic sources of vitamins and minerals. For example, such vitamins are: acerola extracts, rose hips extracts and others, as organic sources of minerals used may be: organic concentrates by seawater, seaweed, eggshell extracts and others. The use of vitamins and minerals may vary to 100% and more than 100%, according to established Recommended Daily Value (RDV) for vitamins and minerals.

In certain embodiments, the present invention beverage containing hydrolyzed collagen may be produced by adding appropriate electrolytes, often categorized as specialized beverage category, such as: isotonic sport beverages, hypertonic sport beverages, and hypotonic sport beverages.

In certain embodiments, additional amino acids may be added to the present invention's beverage. Additional enrichment with amino acids may be done by adding amino acids in their L-forms. For example, L-glutamine, L-isoleucine, L-leucine, L-valine, L-taurine and others may be added to the present invention's beverage. Additionally, amino acids may be added as separate amino acids as well as in combination to other amino acids.

In certain embodiments, other types of proteins, different than collagen may be added to the present invention's hydrolyzed collagen containing beverage. These proteins may be hydrolyzed proteins with higher or lower molecular weight. For additional enrichment, other proteins may be added to the present invention, such as proteins from vegetable as well as animal origin proteins. For example, proteins from soy, peas, milk, egg and others may be added to the present invention's beverage.

In certain embodiments, the beverage of hydrolyzed collagen does not contain whey protein.

In certain embodiments, the beverage of hydrolyzed collagen does not contain sodium acid sulphate.

In certain embodiments, the beverage of hydrolyzed collagen does not contain citric acid, phosphoric acid, malic acid, tartaric acid or fumaric acid.

In certain embodiments, where other types of proteins and/or protein hydrolysates, other than collagen are added, the total concentration of binding proteins in the beverage should be varied, from 0.001 g/l g/L to 8.44 g/L, which may also be expressed as: 1 ppm to 8440 ppm. In these embodiments, the total protein concentration in the beverage is the sum of all protein sources contained in the beverages, including the added hydrolyzed collagen.

Alternative embodiments of the present invention's beverage may be produced which do not contain lactose but may also include lactose as an individual ingredient or have added compositions which are sources of lactose.

In certain embodiments, the present invention's beverage may include additional added ingredients, such as dairy components which can be different fractions derived from milk. For example: whey proteins, casein, caseinates, etc.) or fractions derived from the colostrum (for example: antibodies, immunoglobulin, growth factors). Stated dairy components include, but are not limited to: lipids, proteins (casein, lactoglobulin), antibodies, minerals and salts (phosphates, calcium, magnesium, sodium, potassium, etc.), Vitamins (A, $B_6$, $B_{12}$, D, K, E, thiamine, niacin, biotin, pantothenic acid, etc.), carbohydrates (lactose), enzymes and others.

In certain embodiments, the present invention's beverage may be produced with other additives such as; fresh milk, reconstituted milk or milk fermented with lactic acid cultures and accordingly each of the following types of milk can be skimmed or whole to various extend. Fermented milk is usually derived from using the following starters: *Streptococcus thermophilus ħ Lactobacillus delbrueckii* subsp. *Bulgaricus*, as well as various starters mostly from the *Lactobacillus, Lactococcus, Bifidobacterium* and Str. *Thermophilus* kinds. During fermentation probiotic cultures may be added. Pre-prepared probiotic concentrates (probiotics) may also be added as individual ingredients to the present invention's beverage. The present invention's beverage containing hydrolyzed collagen may also contain added prebiotic ingredients which are fibers which can be soluble as well as insoluble.

In certain embodiments, various other ingredients with beneficial properties may be added to the present invention's beverage containing hydrolyzed collagen. Such ingredients may add value to the present invention's beverage containing hydrolyzed collagen. All these additional healthy ingredients may vary in different combinations as may be individually added to beverages containing hydrolyzed collagen or be combined. Examples for such healthy ingredients are:

L-carnitine,
Coenzyme Q10,
Omega 3 and Omega 6 essential fatty acids,
Bee products, such as natural honey, bee pollen, royal jelly, propolis,
Vegetable extracts from plants with healthy effects that may include various parts of plants as: fruit, blossoms, peels, roots, stables. For example, plants with healthy effects are: Panax Ginseng, Camomila, Lavender, Elettaria cardamomum, Ginkgo biloba and others,
Tea extracts (black, green, white etc.)
Soy isoflavones,
Hyaluronic acid and/or its salts,
Alpha Lipoic Acid,
Extracts of seaweed as well as purified finely ground seaweed,
Mushrooms extracts, edible and special types such as: Lentinula edodes, Grifola frondosa, Cordyceps Sinensis, Hericium erinaceus, Coprinus comatus and others,
Extracts of polyphenols—resveratrol, astaxanthin,
Carotenoids, including lutein and zeaxanthin,
Green coffee extracts,
Caffeine.

Figure 4:
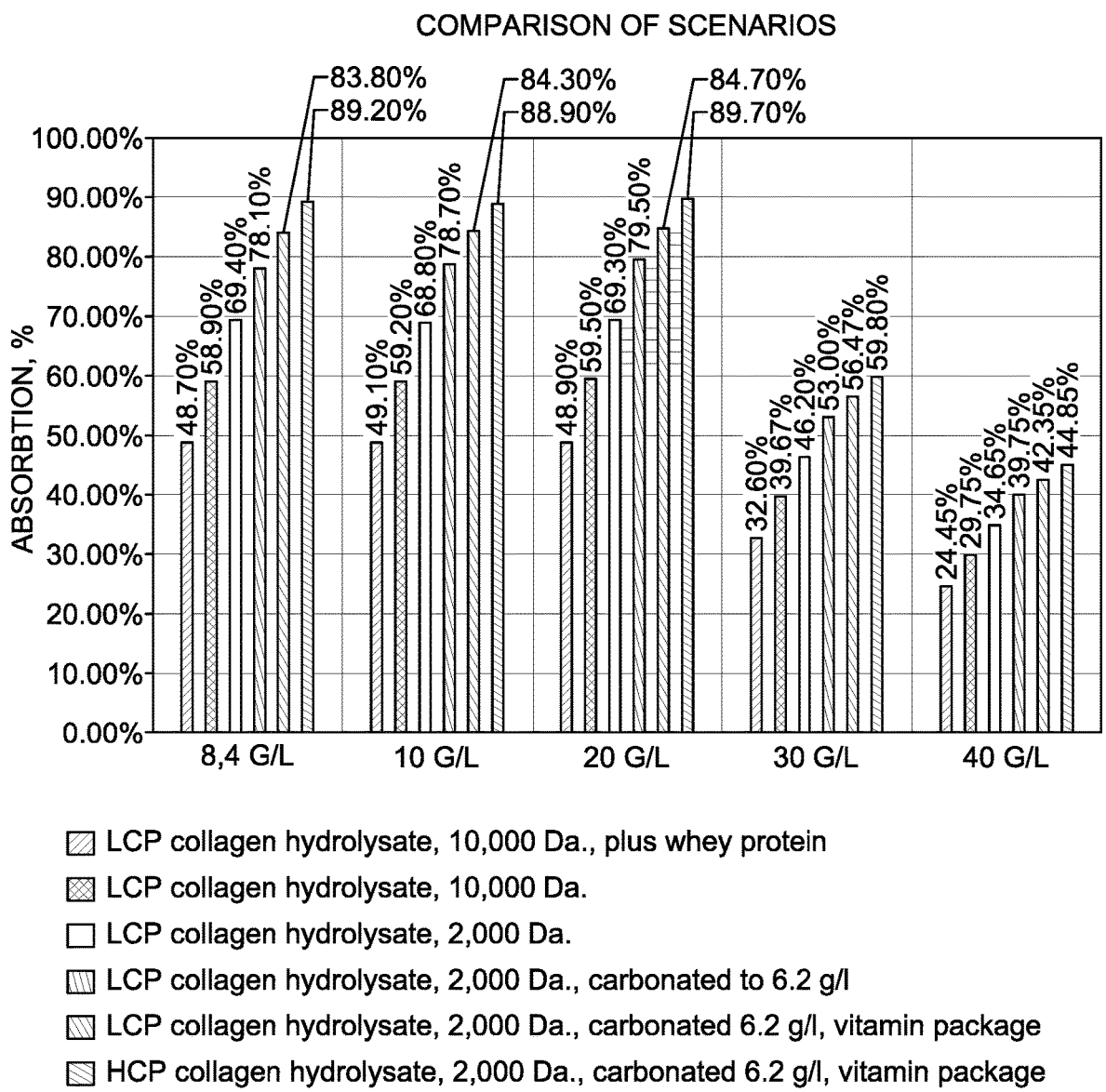
FIG. 4 shows exemplary comparisons of the effect of different concentrations of various collagen hydrolysate compositions on absorption.

As shown in FIGS. 3 and 4, the optimal concentration for the absorption of a 10,000 Dalton collagen hydrolysate was 8.44 g/l with or without whey protein. In contrast, the optimal concentration for the absorption of 2,000 Dalton collagen hydrolysate was 20 g/l if the whey protein was removed and replaced with additives, including a vitamin package as defined herein and/or $CO_2$ and/or pro-hyp/hyp-gly. In all instances tested, the % absorption of the 2000 Dalton collagen hydrolysate decreased at concentrations greater than 20 g/l.

EXAMPLES OF PREFERRED EMBODIMENTS

Example 1

EXAMPLE 1 (as shown in TABLE 1) comprises a cloudy, coloured beverage containing hydrolyzed collagen. The ingredients expressed in weight percentage are listed below in Table 1. Used ingredients are as follows: water purified by ultrafiltration technology, Hydrolyzed bovine collagen Peptan® B 5000HD (Rousselot Inc.), crystalline fructose, peach aroma, citric acid [E330], antioxidant: ascorbic acid, acidity regulator: sodium citrates [E331], a powder mix of vitamins and minerals: D-pantothenate calcium; Pyridoxine hydrochloride; Hydroxocobalamin, D-biotin; Calcium gluconate; Magnesium gluconate; Zinc chloride, RDV levels: Pantothenic acid—15%; Vitamin $B_6$—15%; Vitamin $B_{12}$—15%; Biotin—15%; Ca—15%; Mg—15%; Zn—15%), clear concentrated peach juice, carrageenan [E407], guar gum [E412], colour: carotenes. The beverage is aseptically filled into plastic disposable bottles 375 ml (12.680 fl. oz). It is sterilized in UHT-sterilizer at 137° C. for 4.2 seconds. It has a shelf life of 12 months when stored at 25° C., after opening shall be kept in the refrigerator up to 48 hours.

TABLE 1

| Ingredients: | % w/w in the Beverage |
|---|---|
| Water | 90.16 |
| Hydrolysed bovine collagen Peptan ® B 5000HD | 0.30 |
| Crystalline fructose | 7.50 |
| Peach aroma | 0.12 |
| Citric acid (E330) | 0.15 |
| Ascorbic acid (E300) | 0.05 |
| Sodium citrate (E331) | 0.10 |
| a powder mix of vitamins and minerals | 0.01 |
| Clear peach concentrate (65° Bx) | 1.50 |
| Carrageenan (E407) | 0.05 |
| Guar gum (E412) | 0.05 |
| Colour: carotenes (E160a) | 0.01 |
| Total: | 100% |

Example 2

Example 2 (as shown in Table 2) comprises a clear, colourless beverage containing hydrolyzed collagen. The ingredients, expressed in weight percentages, are listed below in Table 2. Used ingredients are as follows: water purified by ultrafiltration technology, Hydrolyzed bovine collagen Peptan® B 5000HD (Rousselot Inc.). The beverage is aseptically filled into plastic disposable bottles 375 ml (12.680 fl. oz). It is sterilized in UHT-sterilizer at 137° C. for 4.2 seconds. It has a shelf life of 12 months when stored at 25° C., after opening shall be kept in the refrigerator up to 48 hours.

TABLE 2

| Ingredients: | % w/w in the Beverage |
|---|---|
| Water | 99.90 |
| Hydrolysed bovine collagen Peptan ® B 5000HD | 0.10 |
| Total: | 100% |

Example 3

EXAMPLE 3 (as shown in Table 3) comprises an opaque, coloured beverage, containing hydrolyzed collagen. The compositions, expressed in weight percentages, are listed below in Table 3. Used ingredients are as follows: water purified by ultrafiltration technology, Hydrolyzed fish collagen Peptan® F 2000HD (Rousselot Inc.), crystalline fructose, white crystal sugar, natural peach aroma, natural mango aroma, natural guava aroma, amidated pectin [E440ii], citric acid [E330], antioxidant ascorbic acid [E300], acidity regulator: calcium lactate [E327], peach puree single strength, concentrated mango puree, colour: Riboflavins [E101]. The beverage is aseptically filled into disposable plastic bottles 375 ml (12.680 fl. oz). It is homogenized at 150 bar and sterilized in UHT-sterilizer at 137° C. for 4.2 seconds. It has a shelf life of 12 months when stored at 25° C., after opening shall be kept in the refrigerator up to 48 hours.

TABLE 3

| Ingredients: | % w/w in the Beverage |
|---|---|
| Water | 82.53 |
| Hydrolysed fish collagen Peptan ® F 2000HD | 0.40 |
| Crystalline fructose | 6.00 |
| White crystal sugar | 4.50 |
| Peach aroma | 0.10 |
| Mango aroma | 0.15 |
| Guava aroma | 0.05 |
| Citric acid (E330) | 0.16 |
| Ascorbic acid (E300) | 0.05 |
| Calcium lactate (E327) | 0.15 |
| Amidated pectin (E440ii) | 0.20 |
| Peach puree (10° Bx) | 4.50 |
| Mango puree (32° Bx) | 1.20 |
| Colour: Riboflavins (E101) | 0.01 |
| Total: | 100% |

Example 4

EXAMPLE 4 (as shown in Table 4) comprises a transparent, coloured beverage containing hydrolyzed collagen. Ingredients expressed in weight percentage, are listed below in Table 4. Used ingredients are as follows: water purified by ultrafiltration technology, Hydrolyzed fish collagen Peptan® F 2000HD (Rousselot Inc.), crystalline fructose, brown sugar, natural strawberry aroma, natural lime aroma, natural dry green tea extract, citric acid [E330], acidity regulator: sodium citrates, clear strawberry juice concentrate, colour: chlorophyllins [E141]. The beverage is aseptically filled into plastic disposable bottles 375 ml (12.680 fl. oz). It is sterilized in UHT-sterilizer at 137° C. for 4.2 seconds. It has a shelf life of 12 months when stored at 25° C., after opening shall be kept in the refrigerator up to 48 hours.

TABLE 4

| Ingredients: | % w/w in the Beverage |
|---|---|
| Water | 90.33 |
| Hydrolysed fish collagen Peptan ® F 2000HD | 0.40 |
| Crystalline fructose | 3.00 |
| Brown sugar | 5.50 |
| Strawberry aroma | 0.15 |
| Citrus (lime) aroma | 0.05 |
| Dry natural green tea extract | 0.15 |
| Citric acid (E330) | 0.14 |
| Sodium citrates (E331) | 0.05 |
| Clear strawberry concentrate (65° Bx) | 0.20 |
| Colour: chlorophyllins (E141) | 0.03 |
| Total: | 100% |

Example 5

EXAMPLE 5 (as shown in Table 5) comprises an opaque, coloured beverage containing hydrolyzed collagen. The ingredients, expressed in weight percentages, are listed below in Table 5. Used ingredients are as follows: water purified by ultrafiltration technology, Hydrolyzed bovine collagen Peptan® B 5000HD (Rousselot Inc.), soy protein isolate SUPRO® PLUS 2640 DS (DANISCO), natural mango aroma, natural ripe apple aroma, amidated pectin [E440ii], brown cane sugar, citric acid [E330], antioxidant: ascorbic acid [E300], acidity regulator: calcium lactate [E327], apple puree single strength, saffron extract. The beverage is aseptically filled into disposable plastic bottles 375 ml (12.680 fl. oz). It is homogenized at 150 bar and sterilized in UHT-sterilizer at 137° C. for 4.2 seconds. It has a shelf life of 12 months when stored at 25° C., after opening shall be kept in the refrigerator up to 48 hours.

TABLE 5

| Ingredients: | % w/w in the Beverage |
|---|---|
| Water | 83.98 |
| Hydrolysed bovine collagen Peptan ® B 5000HD | 0.30 |
| Soy protein isolate SUPRO ® PLUS 2640 DS | 0.45 |
| Mango aroma | 0.10 |
| Apple aroma | 0.15 |
| Amidated pectin (E440ii) | 0.20 |
| Brown sugar | 9.00 |
| Citric acid (E330) | 0.12 |
| Ascorbic acid (E300) | 0.05 |
| Calcium lactate (E327) | 0.13 |
| Apple puree (10.5° Bx) | 5.50 |
| Saffron extract | 0.02 |
| Total: | 100% |

Example 6

A preferred alternative embodiment of the present invention's beverage comprises a clear, colourless beverage containing hydrolyzed collagen, with vitamins and minerals as shown in Table 6.

TABLE 6

| Ingredients: | % w/w in the Beverage |
|---|---|
| Water | 96.15 |
| Hydrolysed bovine collagen Peptan ® B 5000HD | 0.29 |
| Crystalline fructose | 3.44 |
| Givodan ® Peach nectarine flavour "99278-DO" | 0.04 |
| Citric acid (E330) | 0.12 |
| * a powder mix of vitamins and minerals | 0.37 |
| Total: | 100% |

* Vitamin Premix Material-No. UF40105368; produced by DSM Nutritional Products Europe Ltd. The Vitamin Premix to covers 15% RDA/100 ml of: Vitamin B12, Mg and Zn.

Example 7

An alternative preferred embodiment of the beverage comprises a clear, colourless beverage containing hydrolyzed collagen, with vitamins and minerals as shown in Table 7.

TABLE 7

| Ingredients: | % w/w in the Beverage |
|---|---|
| Water | 96.10 |
| Hydrolysed bovine collagen Peptan ® B 5000HD | 0.29 |
| Crystalline fructose | 3.44 |
| Givodan ® Elder-flower flavour "L-18646" | 0.04 |
| Givodan ® Cucumber flavour "L-130672" | 0.05 |
| Citric acid (E330) | 0.12 |
| * a powder mix of vitamins and minerals | 0.37 |
| Total: | 100% |

* Vitamin Premix Material-No. UF40105368; produced by DSM Nutritional Products Europe Ltd. The Vitamin Premix to covers 15% RDA of: Vitamin B12, Mg and Zn.

Example 8

An alternative preferred embodiment of the beverage comprises a clear, colourless beverage containing hydrolyzed collagen, with vitamins and minerals as shown in Table 8.

TABLE 8

| Ingredients: | % w/w in the Beverage |
|---|---|
| Water | 96.47 |
| Hydrolysed bovine collagen Peptan ® B 5000HD | 0.29 |
| Crystalline fructose | 3.44 |
| Givodan ®Ginger &Lemon flavour "L-147773" | 0.05 |
| Citric acid (E330) | 0.12 |
| * a powder mix of vitamins and minerals | 0.04 |
| Total: | 100% |

* Vitamin Premix Material-No. UF40107368; produced by DSM Nutritional Products Europe Ltd. The Vitamin Premix to covers 15% RDA of: Vitamin B12, Vitamin B7 and Zn.

Example 9

An alternative preferred embodiment of the beverage comprises a clear, colourless beverage containing hydrolyzed and mineral water as shown in Table 9.

TABLE 9

| Ingredients: | % w/w in the Beverage |
|---|---|
| *Mineral water | 99.84 |
| Hydrolysed bovine collagen Peptan ® B 2000HD | 0.1 |
| Phosphoric acid [E338] | 0.059 |
| Total: | 100% |

*The mineral water has the following characteristics:
Electrical conductivity at 20° C.(μS/cm): 493.5;
Potassium (K$^+$), mg/l: 0.60;
Magnesium (Mg$^{2+}$), mg/l: 28.0;
Calcium (Ca$^{2+}$), mg/l: 77.30;
Ammonium (NH$^+$), mg/l: <0.05;
Bicarbonate (HCO$_3^-$), mg/l: 270.0;
Chloride (Cl$^-$), mg/l: 4.60;
Sulphate (SO$_4^{2-}$), mg/l: 65.80;
dry residue at 180° C., mg/l: 340.3

Example 10

Exemplary Method of Preparation:

Collagen powder is mixed with heated water until dissolution. After completion of a filtration step, the concentrated solution is transferred to the second mixing container where other ingredients such as: flavorings, vitamins, minerals etc are added followed by ultra high temperature (UHT) sterilization, quality control and packaging in sterilized bottles.

Example 11

A hydrolyzed collagen beverage with hydrolyzed collagen as the sole protein (no other proteins present in the beverage) presents superior human gastrointestinal absorption of collagen when compared to similarly formulated collagen beverages which include other sources of protein due to the absence of receptor competition. By contrast, the inclusion of one or more additional sources of protein in an otherwise identical hydrolyzed collagen beverage will have reduced efficacy of collagen absorption due to receptor competition among the different protein types.

As shown in FIG. 1A, in the human gastrointestinal tract (GIT), food proteins can be digested into enormous numbers of free amino acids (AAs) and peptides by various digestive enzymes or microbial fermentation. Some of these peptides containing 2-20 AAs have various biological activities and are named bioactive peptides (BAPs). (1) Small peptides can be transported via peptide transporter 1 (PepT1) (2).

Food protein in the lumen is hydrolyzed to peptides by proteases in the brush-border membrane of the small intestine. The peptides may be absorbed (i) via transport across the intestinal epithelial cell monolayers through carrier-mediated routes; (ii), via the paracellular route via tight junctions; (iii) by transcytosis via vesicles; and (iv) via passive transcellular diffusion. For PepT1-mediated transport, peptides are coupled with protons (H+), which are then transported out of the enterocytes by H+/Na+ exchangers. Inside the cells and bloodstream, the peptides may be partly hydrolyzed to amino acids by peptidases. (Adapted from previous reports (3, 4, 5).

Thousands of di- and tripeptides are taken up into enterocytes via PepT1, which is mainly distributed in the intestinal brush-border membrane. PepT1 deficiency in mammals impairs nutrient absorption and causes malabsorption that becomes visible on high protein and high fat feeding (6). As mentioned above, PepT1 can transport various small BAPs including Pro-Hyp (PO). Collagen-derived Gly-Pro-Hyp (GPO) is hydrolyzed by intestinal mucosal apical proteases and the resulting dipeptide PO is transported across the intestinal membrane via PepT1 (7). Shimizu et al. (8) demonstrated that collagen peptides (GAXGLXGP) are transported by energy-independent passive diffusion.

Figure 1B:
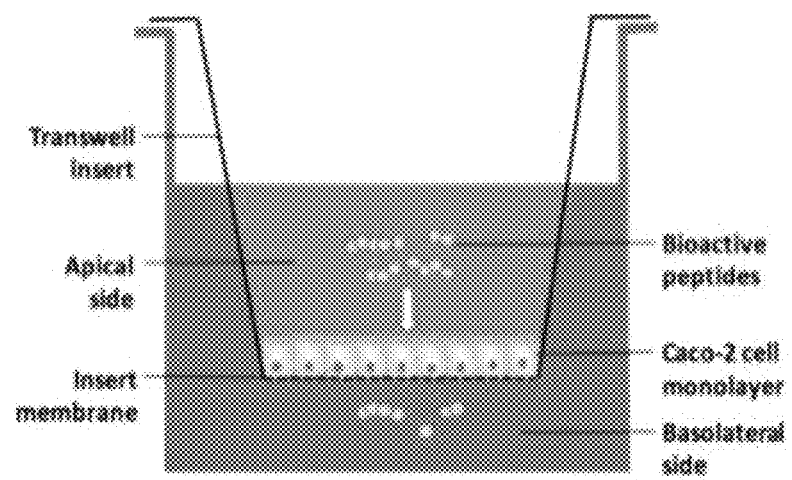
FIG. 1B shows an exemplary embodiment of a transwell assay testing for the transport of collagen peptides across a Caco 2 cell monolayer.

As shown in FIGS. 1B and 1C, at low BAP, concentrations (≤Km), PepT1 is the major contributor to the total transport rate. However, as the BAP concentration increases, the contribution of passive transport becomes more apparent. Because PepT1-mediated transport is saturated at $V_{max}$, all further increases in the total transport rate are attributable to passive transport.

Accordingly, it may be concluded that the presence of other (non-collagen) low molecular weight peptides in a hydrolyzed collagen beverage would competitively and adversely reduce the rate and efficiency of absorption of the collagen peptides that are present.

Cited References
1. Xu, Q., Hong, H., Wu, J., & Yan, X. (2019). Bioavailability of bioactive peptides derived from food proteins across the intestinal epithelial membrane: A review. Trends in food science & technology.
2. Daniel, H. (2004). Molecular and integrative physiology of intestinal peptide transport. Annu. Rev. Physiol., 66, 361-384.
3. Gilbert, E. R., Wong, E. A., & Webb Jr, K. E. (2008). Board-invited review: peptide absorption and utilization: implications for animal nutrition and health. Journal of animal science, 86(9), 2135-2155.
4. Wada, Y., & Loennerdal, B. (2014). Bioactive peptides derived from human milk proteins—mechanisms of action. The Journal of nutritional biochemistry, 25(5), 503-514.
5. Xu, Q., Fan, H., Yu, W., Hong, H., & Wu, J. (2017). Transport study of egg-derived antihypertensive peptides (lkp and iqw) using caco-2 and ht29 coculture monolayers. Journal of agricultural and food chemistry, 65(34), 7406-7414.
6. Daniel, H., & Zietek, T. (2015). Taste and move: glucose and peptide transporters in the gastrointestinal tract. Experimental physiology, 100(12), 1441-1450.
7. Aito, Inoue, M., Lackeyram, D., Fan, M. Z., Sato, K., & Mine, Y. (2007). Transport of a tripeptide, Gly-Pro-Hyp, across the porcine intestinal brush-border membrane. Journal of peptide science: an official publication of the European Peptide Society, 13(7), 468-474.
8. Shimizu, K., Sato, M., Zhang, Y., Kouguchi, T., Takahata, Y., Morimatsu, F., & Shimizu, M. (2010). The bioavailable octapeptide Gly-Ala-Hyp-Gly-Leu-Hyp-Gly-Pro stimulates nitric oxide synthesis in vascular endothelial cells. Journal of agricultural and food chemistry, 58(11), 6960-6965.

Example 12

A peptide weight of 2,000 Daltons is the optimal level for collagen peptides in hydrolyzed collagen beverage. Generally smaller peptides are superior for absorption of hydrolyzed collagen because less energy is required for this energy-dependent process. However, 2,000 Da. is at or very near the optimal weight because the energy absorption savings achieved by further reducing peptide weight significantly below 2,000 Da. would be minimal.

Hou et al. demonstrated that collagen polypeptides had good moisture absorption and retention properties, and collagen polypeptide fractions CP2 (Mr<2 kDa) was better than collagen polypeptide fractions CP1 (2 kDa<Mr<6 kDa). Ultraviolet radiation could cause skin photodamage and collagen polypeptide could alleviate the damage induced by UV radiation. The action mechanisms of collagen polypeptide mainly involved enhancing immunity, reducing the loss of moisture and lipid, promoting antioxidative properties, inhibiting the increase of glycosaminoglycans, repairing endogenous collagen and elastin protein fibres, and maintaining the ratio of type III to type I collagen (1).

The use of collagen hydrolysates (CHs) as a nutraceutical agent in skin aging has gained increasing attention. Here, the effects of various doses and molecular weights of CH from silver carp skin on photoaging in mice were investigated. The ingestion of CH at 50, 100 and 200 mg per kg body weight led to a dose-dependent increase in the hydroxyproline, hyaluronic acid and moisture contents of the skin, but it had no significant effect on the mice body weight, or on the spleen or thymus index. Furthermore, ingesting CH with lower (LMCH, 200-1000 Da, 65%) and higher molecular weight (HMCH, >1000 Da, 72%) significantly increased the skin components and improved the antioxidative enzyme activities in both serum and skin (p<0.05); LMCH performed better than HMCH. By contrast, gelatin (>120 kDa) ingestion did not bring a significant change compared to model mice. These results indicated that LMCH exerted a stronger beneficial effect on the skin than did either HMCH and gelatin, which supported the feasibility of using LMCH as a dietary supplement from silver carp skin to combat photoaging. (2). The CPs (200 Da), used in the H Song et al. study, has been demonstrated to have a stronger beneficial effect on the aging skin than other collagen hydrolysates (including gelatin and CPs with higher molecular weight >1000 Da) (2,3).

E. Proksch et al. conducted a monocentric, double-blinded, randomized, placebo-controlled supplementation study on the effects of a specific CH with molecular weight of 2.0 kDa. The results clearly revealed that oral intake of the specific CH had a beneficial effect on skin physiology, as indicated by increased skin elasticity after 4 weeks of daily consumption. The observed effect was statistically significant (p<0.05) after 4 and 8 weeks in the treatment groups compared to placebo. (4)

In a placebo controlled clinical trial J Asserin et al. found that oral supplementation with fish collagen peptides (Peptan®F molecular weight of 2000 Da.) in women increased the collagen density in the dermis by 9%, as measured by high frequency ultrasound; highly efficaciously increased the amount of water-binding glycosaminoglycans; the collagen content of human skin improved skin hydration as well as the density and structure of the collagen network of the dermis. (5)

Some in vitro studies have demonstrated that Pro-Hyp and Hyp-Gly exert chemotaxis on dermal fibroblasts and enhance cell proliferation. Additionally, Pro-Hyp enhances the production of hyaluronic acid by dermal fibroblasts. These findings suggest that the amounts of Pro-Hyp and Hyp-Gly in blood are important factors to show the efficacy of collagen hydrolysates on skin health. Some study demonstrated that the use of the collagen hydrolysate with a higher content of Pro-Hyp and Hyp-Gly led to more improvement in facial skin conditions, including facial skin moisture, elasticity, wrinkles and roughness. (6)

Studies by Naoki Ito et. al. suggest the possibility for the use of collagen peptide and ornithine to improve skin conditions by increasing plasma IGF-1 levels—the used weight of the collagen peptide was 2000 Da. (7)

All studies with mice showed no significant differences in final body weight between the comparison groups. There are some studies on the effectiveness of lower molecular weight collagen peptides, but the most studied and confirmed effect on skin relates to collagen is weighing 2000 Da. Accordingly, it is logical to conclude that 2,000 Da. is at or very near the optimal peptide weight in respect of a beverage of simple hydrolyzed collagen and water without additives or supplements because the energy absorption savings achieved by further reducing peptide weight significantly below 2,000 Da. would be minimal.

In addition, it is logical to consider the possibility to concentrating collagen with a higher content of Pro-Hyp and Hyp-Gly. A higher content of Pro-Hyp and Hyp-Gly could be expected to result in a measurable increase in the optimal peptide weight.

Cited References
1. Hou, H., Li, B., Zhang, Z., Xue, C., Yu, G., Wang, J., ... & Su, S. (2012). Moisture absorption and retention properties, and activity in alleviating skin photodamage of collagen polypeptide from marine fish skin. *Food chemistry*, 135(3), 1432-1439.
2. Song H, Meng M, Cheng X, et al The effect of collagen hydrolysates from silver carp (*hypophthalmichthys molitrix*) skin on UV-induced photoaging in mice: molecular weight affects skin repair. Food Funct. 2017; 8: 1538-46.
3. Song, H., Zhang, L., Luo, Y., Zhang, S., & Li, B. (2018). Effects of collagen peptides intake on skin ageing and platelet release in chronologically aged mice revealed by cytokine array analysis. *J. Cell. Mol. Med*, 22(1), 277-288.
4. Proksch, E., Segger, D., Degwert, J., Schunck, M., Zague, V., & Oesser, S. (2014). Oral Supplementation of Specific Collagen Peptides Has Beneficial Effects on Human Skin Physiology: A Double-Blind, Placebo-Controlled Study. *Skin Pharmacol Physiol*, 27, 47-55.
5. Asserin, J., Lati, E., Shioya, T., & Prawitt, J. (2015). The effect of oral collagen peptide supplementation on skin moisture and the dermal collagen network: evidence from an ex vivo model and randomized, placebo-controlled clinical trials. *Journal of cosmetic dermatology*, 14(4), 291-301.
6. Inoue, N., Sugihara, F., & Wang, X. (2016). Ingestion of bioactive collagen hydrolysates enhance facial skin moisture and elasticity and reduce facial ageing signs in a randomized double-blind placebo-controlled clinical study. *Journal of the Science of Food and Agriculture*, 96(12), 4077-4081.
7. Ito, N., Seki, S., & Ueda, F. (2018). Effects of Composite Supplement Containing Collagen Peptide and Ornithine on Skin Conditions and Plasma IGF-1 Levels—A Randomized, Double-Blind, Placebo-Controlled Trial. *Marine drugs*, 16(12), 482.

Example 13

Carbonation Improves Absorption of a Hydrolyzed Collagen Beverage.

Introducing CO2 to hydrolyzed collagen beverage can materially increase collagen abortion by slowing the natural increase the pH level in the gastrointestinal system during the digestive process. Typical carbonated beverages such as ordinary soda water and Coca-Cola contain approximately 6.2 grams/liter of CO2 on average.

Gastrointestinal (GI) digestion of a dietary protein is influenced by the physicochemical characteristics of the protein. A complex combination of mechanical, physico-chemical, and physiological processes is involved in the GI digestion of proteins in humans. Digestion of dietary proteins in the gastrointestinal system involves stomach and intestinal proteolytic enzymes. The protein digestion begins in the stomach, where pepsin breaks down the protein into smaller peptides. Pepsin exhibits maximum activity at acidic pH 2.0 and is inactivated at pH 6.5 in the duodenum. The pH in the duodenum is gradually increased to 5-7.5, due to the secretion of bicarbonate and pancreatic juices. The increased pH inactivates the gastric enzymes and gives the optimal activity of the duodenal enzymes (trypsin/chymotrypsin). When the semidigested peptide mix reaches the duodenum, the intestinal enzymes continue to break down the peptides. The final stage of digestion of proteins occurs on the surface of intestinal enterocytes by brush border enzymes, where peptides are hydrolyzed to amino acids as well as di- and tripeptides. The nutrients are then absorbed by the enterocytes of the jejunum and ileum and can be further degraded by intracellular proteases before entering the blood stream. (1)

At standard temperature and pressures, about 1 ml (2 mg) of carbon dioxide dissolves in 1 ml of neutral solution (pH=7). In alkaline solutions, the gas is converted into carbonates and bicarbonates, and it is in this form that any ingested carbon dioxide is likely to be present in the intestinal tract. In general, one can assume that the daily average intake of carbon dioxide in food is equivalent to approximately 1 g daily of sodium bicarbonate or carbonate and therefore represents only a very small fraction of the amounts of these compounds in normal diets (2). In the past, several studies demonstrated that carbon dioxide plays a major role in the process of hydrochloric acid formation and secretion in the parietal cells of the gastric mucosa, after drinking carbonated beverages some of the carbon dioxide may be absorbed through the gastric wall, partly contributing, together with the carbon dioxide from the interstitial fluid and plasma, to the formation of hydrochloric acid. (3)

No evidence has been found that the addition of carbon dioxide to the GI while collagen peptides are present affects the peptides molecular weight. However, a hydrolyzed collagen beverage to which carbonation has been included to a level of 6.2 g/l can be expected to materially slow the normal increase in pH in the GI during the absorption process. Accordingly, the introduction of CO2 at 6.2 g/l will significantly extend the time period during which the pH level in the GI remains below 6.5 pH, thereby increasing the overall efficacy and rate of absorbtion of collagen peptides in the GI.

Cited References
1. Tapal, A., & Tiku, P. K. (2019). Nutritional and Nutraceutical Improvement by Enzymatic Modification of Food Proteins. In Enzymes in Food Biotechnology (pp. 471-481). Academic Press.
2. Select committee on GRAS Substances Evaluation of the health aspects of carbonates and bicarbonates as food ingredients (SCOGS-26) Life Sciences Research Office, Federation of American Societies for Experimental Biology, Bethesda (1975)
3. Cuomo, R., Sarnelli, G., Savarese, M. F., & Buyckx, M. (2009). Carbonated beverages and gastrointestinal system: between myth and reality. Nutrition, Metabolism and Cardiovascular Diseases, 19(10), 683-689.

Example 14

Using Plant-Based Collagen

Usage of a plant-based collagen source can be expected to provide certain health benefits. However, there is not evidence that plant-based collagen course (as opposed to animal-based) improves the absorption of collagen in the gastrointestinal system.

Gorissen et al observed that plant-based proteins have relatively low essential amino acid and leucine contents when compared with animal-based proteins and human skeletal muscle protein. In addition, some but not all plant-based protein isolates are low in lysine and/or methionine contents. As there is a large variability in amino acid composition among the various plant-based protein sources, a balanced combination of different plant-based proteins may provide a higher quality protein blend. (1) Plant-based diets are known to (i) improved plasma lipid concentrations, (ii) reduce blood pressure, and (iii) as part of a lifestyle intervention, the regression of atherosclerotic lesions. (2, 3) At the same time, Vliet et al. provided evidence that some plant proteins produce a lower muscle protein synthetic response compared to animal-based proteins (4).

In conclusion, there is evidence of health benefits from consumption of plant-based proteins including collagen. However, there is no evidence that utilization of plant-based collagen in a hydrolyzed collagen beverage instead of animal-based collagen improves the rate or efficacy of collagen absorption in the human gastrointestinal system.

Cited References
1. Gorissen, S. H., Crombag, J. J., Senden, J. M., Waterval, W. H., Bierau, J., Verdijk, L. B., & van Loon, L. J. (2018). Protein content and amino acid composition of commercially available plant-based protein isolates. Amino acids, 50(12), 1685-1695.
2. Najjar, R. S., Moore, C. E., & Montgomery, B. D. (2018). A defined, plant-based diet utilized in an outpatient cardiovascular clinic effectively treats hypercholesterolemia and hypertension and reduces medications. Clinical cardiology, 41(3), 307-313.
3. Najjar, R. S., Moore, C. E., & Montgomery, B. D. (2018). Consumption of a defined, plant-based diet reduces lipoprotein (a), inflammation, and other atherogenic lipoproteins and particles within 4 weeks. Clinical cardiology, 41(8), 1062-1068.
4. van Vliet, S., Burd, N. A., & van Loon, L. J. (2015). The skeletal muscle anabolic response to plant-versus animal-based protein consumption. The Journal of nutrition, 145(9), 1981-1991.

Example 15

Addition of Certain Vitamins and Minerals (Vitamin Package[1]).

[1] Vitamin Package: magnesium, manganese, pyridoxine/B6, cobalamin/B12, and ascorbic acid The inclusion of certain targeted vitamins and minerals in hydrolyzed collagen beverage can improve absorption of collagen peptides in the gastrointestinal system and can improve efficacy of collagen that has been absorbed. It can be concluded that following vitamins and minerals provide significant improvements:

Magnesium
Manganese
pyridoxine (Vitamin B6)
cobalamin (Vitamin B12)
ascorbic acid (Vitamin C)

Addition of Magnesium

Magnesium stimulates collagen synthesis expressed by fibroblasts in culture. Magnesium inhibits prolyl and lysyl hydroxylases and could be considered as antifibrotic. Magnesium is associated with elastin and plays a protective role in maintaining the extensibility of elastin. Magnesium associated proteoglycans in cartilage prevent the swelling and degradation of this tissue. Magnesium regulates the functional activity of integrins (1, 2, 3)

Studies suggest the presence of overall skin improvement in the use of Magnesium independently. This improvement was not demonstrated to be due to its effect on the absorption of collagen peptides. However, as Magnesium has been shown to stimulate collagen synthesis expressed by fibroblasts in culture, consumption of magnesium concurrently with hydrolyzed collagen can improve the net efficacy of orally ingested hydrolyzed collagen.

Addition of Manganese

Manganese (Mn) is an essential metal that is critical for human health. It is the fifth most abundant metal and twelfth most abundant element overall on earth. Mn is involved in several significant physiological processes, including development, reproduction, immune function, energy metabolism, and antioxidant defenses. Mn is an essential micronutrient that is required for the activity of a diverse set of enzymatic proteins (1). Adult humans absorb approximately 3-5% of ingested Mn. Ingested Mn is readily absorbed in the intestine (2). Studies using the Caco-2 intestinal cell line describe a biphasic uptake process in which Mn transport achieves a steady-state condition after a brief period of equilibration between intracellular and extracellular components (3). Prolidase is metalloprotease, requiring manganese for catalytic activity, an enzyme involved in collagen metabolism, cleaves imidodipeptides containing C-terminal proline, providing large amount of proline for collagen synthesis. (4).

Among the multilayered and interdependent antioxidant system, which consists of non-enzymatic as well as enzymatic components, the mitochondrial superoxide dismutase 2 (SOD2, MnSOD) is a subject of particular interest, as it is located in the mitochondrial matrix where it represents the first line of antioxidant defense against superoxide anions produced as byproducts of oxidative phosphorylation. MnSOD overexpressing fibroblast populated collagen lattices revealed a significantly enhanced contraction compared to collagen lattices populated with vector control cells (5). Manganese is needed for producing the amino acid proline, which is essential for collagen formation and wound healing in human skin cells. Manganese plays an important role in the formation of collagen in skin cells (6).

1. Horning K J, Caito S W, Tipps K G, Bowman A B, Aschner M. Manganese Is Essential for Neuronal Health. *Annu Rev Nutr*. 2015; 35:71-108. doi: 10.1146/annurev-nutr-071714-034419. Epub 2015 May 13. PMID: 25974698; PMCID: PMC6525788.
2. Finley J W, Johnson P E, Johnson L K. 1994. Sex affects manganese absorption and retention by humans from a diet adequate in manganese. Am. J. Clin. Nutr 60:949-55
3. Leblondel G, Allain P. 1999. Manganese transport by Caco-2 cells. Biol. Trace Element Res 67:13-28
4. Myara, I., Charpentier, C., Lemonnier, A., 1982. Optimal conditions for prolidase assay by proline colorimetric determination: application to imidodipeptiduria. Clin. Chim. Acta 125, 193-205.
5. Wenk J, Brenneisen P, Wlaschek M, Poswig A, Briviba K, Oberley T D, et al. Stable overexpression of manganese superoxide dismutase in mitochondria identifies hydrogen peroxide as a major oxidant in the AP-1-mediated induction of matrix-degrading metalloprotease-1. *J Biol Chem* 1999; 274:25869-76.
6. Park K. Role of micronutrients in skin health and function. Biomol Ther (Seoul). 2015 May; 23(3):207-17. doi:

10.4062/biomolther.2015.003. Epub 2015 May 1. PMID: 25995818; PMCID: PMC4428712.

Addition of Pyridoxine (Vitamin B6)

Studies demonstrate that pyridoxine (B6) induces a positive influence on human keratinocytes and fibroblasts. In particular, pyridoxine promotes fibroblast migration. Further, a statistically significant induction of keratinocyte proliferation is observed with in conjunction with human ingestion of pyridoxine. (4, 5).

Addition of Cobalamin (Vitamin B12)

Cobalamin (B12) is a naturally occurring organometallic compound containing cobalt that serves as an important water-soluble vitamin for human health. The recommended daily intake for cobalamin is 2.4 µg (6). This vitamin functions as a cofactor for two classes of human enzymes, namely, isomerases and methyltransferases. Consequently, cobalamin deficiency can cause disturbances in cell division, leading to neuropathy, nervous system disease and pernicious anemia. Vitamin B12 deficiency is common in people of all ages who consume a low intake of animal-source foods, including populations in developing countries. It is also prevalent among the elderly, even in wealthier countries, due to their malabsorption of B12 from food. (7).

Altered cobalamin levels can lead to dermatological manifestations, which may indicate a deficiency or excess of this vitamin. The biochemistry and metabolism of cobalamin is complex, and diseases can be associated with alterations of this metabolic pathway. The cutaneous manifestations of cobalamin deficiency include hyperpigmentation (most commonly); hair and nail changes; and oral changes, including glossitis. Additionally, several dermatologic conditions, including vitiligo, aphthous stomatitis, atopic dermatitis, and acne are related to cobalamin excess or deficiency. (8)

The addition of cobalamin can improve the skin condition, however, was not carried out research studying the impact of cobalamin on the absorption of peptides, on the contrary discovered that whey protein can improve the absorption of cobalamin. (9, 10)

Addition of Vitamin C (Ascorbic Acid)

Several studies have shown that the presence of ascorbic acid (Vitamin C) can increase the natural collagen production of the body (12, 13, 14)

Optimal Concentrations of Targeted Vitamins and Minerals

Dietary reference intakes are set of reference values used to plan and assess nutrient intakes of healthy people. The Daily Value (DV) is a value published by the US Food and Drug Administration (FDA) containing the recommended intake of specified vitamins and minerals and has been determined sufficient to meet the nutrient requirements of nearly all (97+%) of healthy people without taking into account age and sex.

In general, the concentration of each of the targeted vitamins and minerals (magnesium, manganese, pyridoxine, cobalamin, ascorbic acid) should not exceed 10% of the FDA recommended DV per standard 500 ml. collagen beverage, or 20% of the FDA recommended DV per liter. Higher concentrations of the targeted vitamins are possible. Higher concentration of any of the targeted vitamins and minerals risks formation of sediment and material changes in the taste of the beverage.

TABLE 10

|  | Magnesium mg/d | Manganese mg/d | B12 cg/d | B6 mg/d | Vit. C mg/d |
| --- | --- | --- | --- | --- | --- |
| DV | 400 | 2.0 | 6.0 | 2.0 | 60 |
| 10% DV | 40 | 0.40 | 0.60 | 0.40 | 6.0 |

Example 16

Increased Ratio Pro-Hyp and Hyp-Gly Increases Efficacy of Collagen

Two different types of collagen dipeptides, prolyl-hydroxyproline (Pro-Hyp) and hydroxyprolyl-glycine (Hyp-Gly) form a portion of peptides in hydrolyzed collagen. Both Pro-Hyp and Hyp-Gly are available at high concentrations for several hours in the human bloodstream following oral administration. Some in vitro studies have demonstrated that Pro-Hyp and Hyp-Gly exert chemotaxis on dermal fibroblasts and enhance cell proliferation. Additionally, Pro-Hyp enhances the production of hyaluronic acid by dermal fibroblasts. These findings suggest that the amounts of Pro-Hyp and Hyp-Gly in blood are important factors to show the efficacy of collagen hydrolysates on skin health. Some study demonstrated that the use of the collagen hydrolysate with a higher content of Pro-Hyp and Hyp-Gly led to more improvement in facial skin conditions, including facial skin moisture, elasticity, wrinkles and roughness.

Pro-Hyp and Hyp-Gly may have a low ratio of dipeptide-to-product content, about 0.1 g kg-1 of product (LCP), or it may also have a high ratio of dipeptide-to-product content, greater than 2 g. kg-1 of product (HCP). A recent clinical provides evidence that both LCP and HCP are effective supplements for increasing skin elasticity, reducing wrinkles, improving skin moisture and reducing the feeling of skin dryness and roughness. This study further indicates that HCP provides greater improvement in skin elasticity, increased moisture and reducing wrinkles on facial skin than LCP (16).

Example 17

Modifications Allow Increased Concentration of Collagen. Increased Range:

From 8.44 g./l to 40 g/l. Simple hydrolyzed collagen with a peptide weight of 10,000 Daltons (common in supplements and commercial food products containing collagen) and no further additives can be expected to have an optimal concentration range of approximately 8.44 g/l.

In studies on the absorption, collagen peptides were shown to have a dose-dependent effect and increased concentrations of hydrolyzed collagen increases absorption of collagen peptides with a corresponding increased effect on the skin. In studies on the absorption, collagen peptides were shown to have a dose-dependent effect. (17). However, there is significant evidence of a limit to the saturation of peptides, to a point where a rise in concentration increasingly loses effectiveness. (18) The optimal range for absorption and beneficial effect on skin in respect of simple hydrolyzed collagen with a peptide weight of 10,000 Daltons (common in supplements and commercial food products containing collagen) and containing no further additives can be expected to be approximately than 8.44 g/l. However, the optimal range can be expected to fluctuate with the introduction of additional factors and modifications.

Theoretical calculation of optimal concentration of collagen in hydrolyzed collagen beverage:

TABLE 11

Theoretical Estimated Absorption Rates of Collagen Hydrolysate - % Absorbed

| | Absorption of collagen in % by Concentration | | | | |
|---|---|---|---|---|---|
| | 8.44 g/l | 10 g/l | 20 g/l | 30 g/l | 40 g/l |
| LCP collagen hydrolysate, 10,000 Da. (with whey protein) | 48.7 | 49.1 | 48.9 | 32.6 | 24.4 |
| LCP collagen hydrolysate, 10,000 Da. ** (** = without other proteins) | 58.9 | 59.2 | 59.5 | 39.6 | 29.7 |
| LCP collagen hydrolysate, 2,000 Da ** | 69.4 | 68.8 | 69.3 | 46.2 | 34.6 |
| LCP collagen hydrolysate, 2,000 Da. **, carbonated to 6.2 g/l ** | 78.1 | 78.7 | 79.5 | 53.0 | 39.7 |
| LCP collagen hydrolysate, 2,000 Da. **, carbonated 6.2 g/l, and "Vitamin Package" | 83.8 | 84.3 | 84.7 | 56.4 | 42.3 |
| HCP collagen hydrolysate, 2,000 Da. **, carbonated 6.2 g/l, and "Vitamin Package" | 89.2 | 88.9 | 89.7 | 59.8 | 44.8 |

As shown in TABLE 11, the optimal concentration of collagen is about 20 g/l with at least (1) no whey, (2) a molecular weight of about 2,000 da., (3) a Vitamin Package", and addition of CO2 and pro-hyp/hyp-gly improving absorption further, but not changing the optimal concentration.

CITED REFERENCES

1. Galland, L. D., Baker, S. M., & McLellan, R. K. (1986). Magnesium deficiency in the pathogenesis of mitral valve prolapse. *Magnesium*, 5(3-4), 165-174.
2. Senni, K., Foucault-Bertaud, A., & Godeau, G. (2003). Magnesium and connective tissue. *Magnesium research*, 16(1), 70-74.
3. Sasaki, Y., Sathi, G. A., & Yamamoto, O. (2017). Wound healing effect of bioactive ion released from Mg-smectite. *Materials Science and Engineering: C*, 77, 52-57.
4. Fujii, K., Kajiwara, T., & Kurosu, H. (1979). Effect of vitamin B6 deficiency on the crosslink formation of collagen. *FEBS letters*, 97(1), 193-195.
5. Rembe, J. D., Fromm-Dornieden, C., & Stuermer, E. K. (2018). Effects of vitamin B complex and vitamin C on human skin cells: is the perceived effect measurable? *Advances in skin & wound care*, 31(5), 225-233.
6. B. R. Rucker, J. W. Suttie, B. D. McCormick, L. J. Machilin Handbook of vitamin
7. Marcel Dekker Inc, New York (2001)
8. Allen, L. H. (2010). Bioavailability of vitamin B12. International Journal for Vitamin and Nutrition Research, 80(4), 330.
9. Brescoll, J., & Daveluy, S. (2015). A review of vitamin B12 in dermatology. American journal of clinical dermatology, 16(1), 27-33.
10. Wang, H., Shou, Y., Zhu, X., Xu, Y., Shi, L., Xiang, S., . . . & Han, J. (2019). Stability of vitamin B12 with the protection of whey proteins and their effects on the gut microbiome. Food chemistry, 276, 298-306.
11. Liu, G., Yang, J., Wang, Y., Liu, X., & Chen, L. (2019). Protein-lipid composite nanoparticles for the oral delivery of vitamin B12: Impact of protein succinylation on nanoparticle physicochemical and biological properties. Food Hydrocolloids, 92, 189-197.
12. Paxton, Jennifer Z., Liam M. Grover, and Keith Baar. "Engineering an in vitro model of a functional ligament from bone to bone." Tissue engineering part A 16.11 (2010): 3515-3525
13. Shaw, G., Lee-Barthel, A., Ross, M. L., Wang, B., & Baar, K. (2016). Vitamin C-enriched gelatin supplementation before intermittent activity augments collagen synthesis. The American journal of clinical nutrition, 105(1), 136-143.
14. Lis, D. M., & Baar, K. (2019). Effects of Different Vitamin C-Enriched Collagen Derivatives on Collagen Synthesis. International journal of sport nutrition and exercise metabolism, (00), 1-6.
15. U.S. Department of Health and Human Services, Food and Drug Administration; available https://www.accessdata.fda.gov/scripts/InteractiveNutritionFactsLabel/factsheets/Vitamin_and_Mineral_Chart.pdf.
16. Inoue, N., Sugihara, F., & Wang, X. (2016). Ingestion of bioactive collagen hydrolysates enhance facial skin moisture and elasticity and reduce facial ageing signs in a randomised double-blind placebo-controlled clinical study. *Journal of the Science of Food and Agriculture*, 96(12), 4077-4081.
17. Shigemura, Y., Kubomura, D., Sato, Y., & Sato, K. (2014). Dose-dependent changes in the levels of free and peptide forms of hydroxyproline in human plasma after collagen hydrolysate ingestion. Food chemistry, 159, 328-332.
18. Ohara, H., Ichikawa, S., Matsumoto, H., Akiyama, M., Fujimoto, N., Kobayashi, T., & Tajima, S. (2010). Collagen-derived dipeptide, proline-hydroxyproline, stimulates cell proliferation and hyaluronic acid synthesis in cultured human dermal fibroblasts. The Journal of dermatology, 37(4), 330-338.

While this disclosure refers to exemplary embodiments, it will be understood by those skilled in the art that various changes may be made, and equivalents may be substituted for elements thereof without departing from the scope of the disclosure. In addition, many modifications will be appreciated by those skilled in the art to adapt a particular instrument, situation or material to the teachings of the disclosure without departing from the spirit thereof.

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

What is claimed is:
1. A beverage comprising:
a non-protein portion comprising water, vitamins, and minerals, wherein the vitamins include at least Vitamin B12, Vitamin B6, and Vitamin C, and wherein the minerals comprise at least magnesium and manganese; and a protein portion consisting of collagen and a dipeptide selected from the group consisting of prolylhydroxyproline (Pro-Hyp), hydroxyprolyl-glycine (Hyp-Gly), and combinations thereof, and wherein the collagen is a hydrolyzed collagen that comprises peptides having molecular weights that are less than 2000 Daltons wherein the collagen is isolated from a plant expressing recombinant collagen, wherein the collagen has a concentration range between 1 milligram/liter to about 8440 milligram/liter.

2. The beverage of claim 1, wherein the water is carbonated.

3. The beverage of claim 1, wherein the non-protein portion of the beverage does not comprise sodium acid sulphate.

4. The beverage of claim 1, wherein the non-protein portion of the beverage does not comprise any one of citric acid, phosphoric acid, malic acid, tartaric acid and fumaric acid.

5. The beverage of claim 1, wherein at least one vitamin of the vitamins is in an amount equal to a US "Recommended Daily Allowance (RDA)".

6. The beverage of claim 1, wherein the vitamins further comprise at least one of Vitamin A, Vitamin D, Vitamin E, Vitamin K, Thiamin (Vitamin B 1), Riboflavin (Vitamin B2), Niacin (Vitamin B3), Folic acid (Vitamin B9), Biotin (Vitamin B7), Pantothenic acid (Vitamin B5).

7. The beverage of claim 1, wherein the vitamins further comprise Biotin (Vitamin B7).

8. The beverage of claim 1, wherein the minerals further comprise at least one of Potassium (K), Chloride (CI), Calcium (Ca), Phosphorus (P), Iron (Fe), Zinc (Zn), Copper (Cu), Fluoride (F), Selenium (Se), Chromium (Cr), Molybdenum (Mo) and Iodine (I).

9. The beverage of claim 1, wherein the beverage further comprises one or more ingredients selected from the group consisting of L-carnitine, coenzyme Q10, Omega-3 and Omega-6 fatty acids, honey, bee pollen, royal jelly, propolis, tea extracts, soy isoflavones, hyaluronic acid, alpha lipoic acid, carotenoids, and caffeine.

10. The beverage of claim 1, wherein the beverage further comprises one or more ingredients selected from the group consisting of crystalline fructose, peach aroma, citric acid, ascorbic acid, sodium citrate, d-panthothenate calcium, pyridoxine hydrochloride, hydroxocobalamin, magnesium gluconate, and zinc chloride.

11. The beverage of claim 10, wherein the beverage comprises citric acid.

12. A beverage comprising:
a non-protein portion comprising water, vitamins, and minerals, wherein the vitamins include at least Vitamin B 12, Vitamin B6, and Vitamin C, and wherein the minerals comprise at least magnesium, manganese, and molybdenum; and
a protein portion, wherein the protein portion comprises hydrolyzed collagen, no whey protein, and a dipeptide selected from the group consisting of prolyl-hydroxyproline (Pro-Hyp), hydroxyprolylglycine (Hyp-Gly), and combinations thereof and wherein the hydrolyzed collagen comprises peptides having molecular weights that are less than 2000 Daltons, wherein the collagen has a concentration range between 1 milligram/liter to about 8440 milligram/liter.

13. A method for increasing absorption of hydrolyzed collagen in a digestive tract of a subject in need thereof, wherein the method comprises consuming the beverage of claim 1 by the subject.

* * * * *